US007592023B2

(12) United States Patent
Murphy et al.

(10) Patent No.: US 7,592,023 B2
(45) Date of Patent: *Sep. 22, 2009

(54) TRANSPLANT MEDIA

(75) Inventors: Christopher J. Murphy, Madison, WI (US); Jonathan F. McAnulty, Oregon, WI (US); Ted W. Reid, Lubbock, TX (US)

(73) Assignee: Trophic Solutions LLC, Madison, WI (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/657,851

(22) Filed: Sep. 9, 2003

(65) Prior Publication Data

US 2005/0089836 A1 Apr. 28, 2005

Related U.S. Application Data

(63) Continuation of application No. 09/917,340, filed on Jul. 27, 2001, now Pat. No. 6,696,238.

(60) Provisional application No. 60/290,932, filed on May 15, 2001, provisional application No. 60/249,602, filed on Nov. 17, 2000, provisional application No. 60/221,632, filed on Jul. 28, 2000.

(51) Int. Cl.
*A61K 35/12* (2006.01)
*A61K 38/30* (2006.01)
*A61K 38/00* (2006.01)

(52) U.S. Cl. .................. 424/520; 424/278.1; 530/303; 530/350; 536/16.8

(58) Field of Classification Search .............. 530/303, 530/350, 300; 514/2, 54; 435/7.23
See application file for complete search history.

(56) References Cited

U.S. PATENT DOCUMENTS

| | | | | |
|---|---|---|---|---|
| 4,543,252 | A | 9/1985 | Lehrer et al. | 514/12 |
| 4,659,692 | A | 4/1987 | Lehrer et al. | 514/12 |
| 4,705,777 | A | 11/1987 | Lehrer et al. | 514/12 |
| 4,798,824 | A | 1/1989 | Belzer et al. | 514/60 |
| 4,873,230 | A | 10/1989 | Belzer et al. | 514/60 |
| 5,130,298 | A | 7/1992 | Cini et al. | 514/12 |
| 5,183,805 | A | 2/1993 | Lee et al. | 514/13 |
| 5,210,185 | A | 5/1993 | Della Valle et al. | 530/399 |
| 5,218,093 | A | 6/1993 | Guo et al. | 530/399 |
| 5,410,019 | A | 4/1995 | Coy et al. | 530/323 |
| 5,457,034 | A | 10/1995 | della Valle et al. | 435/69.4 |
| 5,470,828 | A | 11/1995 | Ballard et al. | 514/12 |
| 5,514,536 | A | 5/1996 | Taylor | 435/1.2 |
| 5,639,664 | A | 6/1997 | Iwane et al. | 435/320 |
| 5,650,496 | A | 7/1997 | Brierley et al. | 530/416 |
| 5,696,152 | A | 12/1997 | Southard | 514/449 |
| 5,766,624 | A * | 6/1998 | Janoff et al. | 424/450 |
| 5,792,831 | A | 8/1998 | Maloy | 530/326 |
| 5,834,178 | A * | 11/1998 | Churchill et al. | 435/1.2 |
| 5,998,376 | A | 12/1999 | Witten et al. | 514/15 |
| 6,045,990 | A | 4/2000 | Baust et al. | 435/1.1 |
| 6,172,185 | B1 * | 1/2001 | Hancock et al. | 530/326 |
| 6,214,008 | B1 * | 4/2001 | Illi | 606/77 |
| 6,537,808 | B2 * | 3/2003 | Lambiase | 435/325 |

FOREIGN PATENT DOCUMENTS

WO WO 9960016 A2 * 11/1999

OTHER PUBLICATIONS

The South African Medicines Formulary (2006) J01F Macrolides and Lincosamides, http://web.uct.ac.za/depts/mini/jmoodie/□□j01part3.html, pp. 1-4.*
Kwock et al. (1984) Retention and distribution of iron added to cow's milk and human milk as various salts and chelates. J. Nutr., vol. 114, No. 8, pp. 1456-1461.*
Goldstein et al. (2007) Twinning and higher intake of dairy products, J. Reprod. Med., vol. 52, No. 2, pp. 140-141.*
Hakovirta et al. (2006) Bioassay for nisin in milk, processed cheese, salad dressings, canned tomatoes, and liquid egg products, Appl. Environ. Microbiol., vol. 72, No. 2, pp. 1001-1005.*
Frederick et al. (1931) production of iron in cow milk and human milk, J. Biol. Chem., vol. 92, No. 59, pp. 237-240.*
Raw-milk-facts (2007, updated) "Hormones and growth factors in raw milk", http://www.raw-milk-facts.com/hormones.html., pp. 1-7.*
Petrinec et al. (1996) Insulin-like growth factor-I attenuates delayed graft function in a canine renal autotransplantation model. Surgery, vol. 120, No. 2, pp. 221-225.*
Steffen et al. (1990)Comparison of University of Wisconsin (UW) and Eurocollins (EC) preservation solutions in a rat liver transplant model, Transpl. Int., vol. 3, No. 3, pp. 133-136.*
Chien et al. (2000) Comparison of university of wisconsin, eurocollins, low-potassium dextran, and krebs-henseleit solutions for hypothermic lung preservation, J. Thorac. Cardiovasc. Surg., vol. 119, No. 5, pp. 921-930.*
Hoenicke et al. (2000) Donor heart preservation with a novel hyperpolarizing solution: superior protection compared with University of Wisconsin solution, J. Thorac. Cardiovasc. Surg., vol. 120, No. 4, p. 746-754.*
Caverzasio et al. (1995) Potential role of IGF-1 in parathyroid hormone-related renal growth induced by high protein diet in uninephrectomized rats, Kidney Int., vol. 48, No. 1, pp. 33-38.*
Ortiz et al. (2000) Microcomputed tomography of kidneys following chronic bile duct ligation, Kidney Int., vol. 58, No. 4, pp. 1632-1640.*
Tavakkol et al. (1999) Maintenance of human skin in organ culture: role for insulin-like growth factor-1 receptor and epidermal growth factor receptor, Arch Dermatol Res., vol. 291, No. 12, pp. 643-651.*

(Continued)

*Primary Examiner*—Andrew Wang
*Assistant Examiner*—Samuel Liu
(74) *Attorney, Agent, or Firm*—Casimir Jones, S.C.

(57) ABSTRACT

The present invention relates to media containing purified antimicrobial polypeptides, such as defensins, and/or cell surface receptor binding proteins. The media may also contain buffers, macromolecular oncotic agents, energy sources, impermeant anions, ATP substrates. The media find use for the storage and preservation of internal organs prior to transplant.

12 Claims, 9 Drawing Sheets

OTHER PUBLICATIONS

McAnulty et al. (2002) Successful six-day kidney preservation using trophic factor supplemented media and simple cold storage, Am. J. Transplan., vol. 2, pp. 712-718.*

Chen et al.. "Efficacy of Media Enriched With Nonlactate-Generating Substrate For Organ Preservation," Transplantation 67:800-808 (1999).

Petrinec et al., "Insulin-like growth factor-I attenuates delayed graft function in a canine renal autotransplantation model," Surgery 120:221-226 (1996).

Murphy et al., "Defensins Are Mitrogenic for Epithelial Cells and Fibroblasts," J. of Cellular Physiology 133:408-413 (1993).

Romeo et al., "Structure and Bactericidal Activity of an Antibiotic Dodecapeptide Purified from Bovine Netrophils,"J. of Biological Chemistry 163:9573-9575 (1988).

Reid et al., "Studies on the effect of the bovine neutrophil antibiotic dodeca-peptide (BNP-1) on the viability of human corneal endothelial cells stored in optisol," IOVS 39:S78 (1998).

Sambrook et al., 1989, *Nucleic Acid Hybridization, A Practical Approach*, IRL Press, Washington D.C., 1985. This reference is a book and is not being supplied at this time.

Anderson and Young, Quantitative Filter Hybridization *in Nucleic Acid Hybridization* 73-111 (1985).

*Antibacterial Peptide Protocols*, ed. W. M. Shafer, Humana Press, Totowa, NJ [1997].

Selsted et al., "Purification and ANitbacterial Activity of Antimicrobial Peptides of Rabbit Granulocyes,"Infect. Immun. 45:150-154 [1984].

Zeya et al., "Antimicrobial Specificity of Leukocyte Lysosomal Cationic Proteins," Science 154:1049-1051 [1966].

Zeya et al., "Arginine-Rich Proteins of Polymorphonuclear Leukocyte Lysosomes," J. Exp. Med. 127:927-941 [1968].

Zeya et al., "Chaaracterization of Cationic Protein-Bearing Granules of Polymorphonuclear Leukocytes," Lab. Invest. 24:229-236 [1971].

Lehrer et al., "Fungicidal Components of Mammalian Granulocytes Active against *Cryptococcus neoformans*," J. Infect. Dis. 136:96-99 [1977].

Lehrer et al., "Nonoxidative Fungicidal Mechanisms of Mammalian Granulocytes: Demonstration of Components with Candidacidal Activity o Human, Rabbit, and Guinea Pig Leukocytes," Infect. Immun. 11:1226-1234 [1975].

Lehrer et al., "Direct Inactivation of Viruses of MCP-1 anfd MPC-2, Natural Peptide Antibiotics from Rabbit Leukocytes," J. Virol. 54:467 [1985].

Selsted et al., "Activity of Rabbit Leukocyte Peptides Against *Candida albicans*," Infect. Immun, 49:202-206 [1985].

Segal et al., "In Vitro Effect of Phagocyte Cationic Peptides on *Coccidioides immitis*," J. Infect. Diseases151:890-894 [1985].

Ganz et al., "Natural Peptide Antibiotics of Human Neutrophils," J. Clin. Invest. 76:1427-1435 [1985].

Wilde et al., "Purification and Characterization of Human Neutrophil Peptide 4, a Novel Member of the Defensin Family," J. Biol. Chem. 264:11200-11203 [1989].

Eisenhauer et al., "Purification and Antimicrobial Properties of Three Defenins from Rat Neutrophils," Infection and Immunity 57:2021-2027 [1989].

Selsted et al., "Purification, Primary Structure, and Antimicrobial Activities of a Guinea Pig Neutrophil Defensin,"Infect. lmmun. 55:2281-2286 [1987].

Merrifield et al., "Design and synthesis of antimicrobial peptides," Ciba Found Symp. 186:5-26 (1994).

Wade et al., "All-D amino acid-containing channel-forming antibiotic peptides," Proc. Natl. Acad. Sci. USA 87(12):4761-5 (1990).

Merrifield, "Solid Phase Peptide Syntheis. I. The Synthesis of a Tetrapeptide," J. Am. Chem. Soc. 85:2149-2156 [1963].

Beaucage et al., "Deoxynucleoside Phosphoramidites-A New Class of Key Intermediates for Deoxypolynucleotide Synthesis," Tetra. Lett. 22:1859-1862 [1981].

Rein et al., Computer-Assisted Modeling of Receptor-Ligand Interactions, Alan Liss. N.Y., [1989].

Cary et al., Advanced Organic Chemistry, part B, Plenum Press, New York [1983]. This reference is a book and is not being supplied at this time but if the Examiner requests a copy, it will be provided.

Reid et al., "Stimulation of Epithelial Cell Growth by the Neuropeptide Substance P." J. of Cellular Biochemistry 52:476-485 (1993).

* cited by examiner

SEQUENCE LISTING

```
<160> NUMBER OF SEQ ID NOS: 96

<210> SEQ ID NO 1
<211> LENGTH: 64
<212> TYPE: PRT
<213> ORGANISM: Bos taurus

<400> SEQUENCE: 1

Met Arg Leu His His Leu Leu Leu Ala Leu Leu Phe Leu Val Leu Ser
 1               5                  10                  15

Ala Gly Ser Gly Phe Thr Gln Gly Val Arg Asn Ser Gln Ser Cys Arg
            20                  25                  30

Arg Asn Lys Gly Ile Cys Val Pro Ile Arg Cys Pro Gly Ser Met Arg
        35                  40                  45

Gln Ile Gly Thr Cys Leu Gly Ala Gln Val Lys Cys Cys Arg Arg Lys
    50                  55                  60

<210> SEQ ID NO 2
<211> LENGTH: 24
<212> TYPE: PRT
<213> ORGANISM: Xenopus laevis

<400> SEQUENCE: 2

Gly Val Leu Ser Asn Val Ile Gly Tyr Leu Lys Lys Leu Gly Thr Gly
 1               5                  10                  15

Ala Leu Asn Ala Val Leu Lys Gln
            20

<210> SEQ ID NO 3
<211> LENGTH: 81
<212> TYPE: PRT
<213> ORGANISM: Xenopus laevis

<400> SEQUENCE: 3

Met Tyr Lys Gly Ile Phe Leu Cys Val Leu Leu Ala Val Ile Cys Ala
 1               5                  10                  15

Asn Ser Leu Ala Thr Pro Ser Ser Asp Ala Asp Glu Asp Asn Asp Glu
            20                  25                  30

Val Glu Arg Tyr Val Arg Gly Trp Ala Ser Lys Ile Gly Gln Thr Leu
        35                  40                  45
```

```
Gly Lys Ile Ala Lys Val Gly Leu Lys Glu Leu Ile Gln Pro Lys Arg
         50                  55                  60

Glu Ala Met Leu Arg Ser Ala Glu Ala Gln Gly Lys Arg Pro Trp Ile
65                  70                  75                  80

Leu

<210> SEQ ID NO 4
<211> LENGTH: 303
<212> TYPE: PRT
<213> ORGANISM: Xenopus laevis

<400> SEQUENCE: 4

Met Phe Lys Gly Leu Phe Ile Cys Ser Leu Ile Ala Val Ile Cys Ala
1               5                   10                  15

Asn Ala Leu Pro Gln Pro Glu Ala Ser Ala Asp Glu Asp Met Asp Glu
            20                  25                  30

Arg Glu Val Arg Gly Ile Gly Lys Phe Leu His Ser Ala Gly Lys Phe
        35                  40                  45

Gly Lys Ala Phe Val Gly Glu Ile Met Lys Ser Lys Arg Asp Ala Glu
    50                  55                  60

Ala Val Gly Pro Glu Ala Phe Ala Asp Glu Asp Leu Asp Glu Arg Glu
65                  70                  75                  80

Val Arg Gly Ile Gly Lys Phe Leu His Ser Ala Lys Lys Phe Gly Lys
                85                  90                  95

Ala Phe Val Gly Glu Ile Met Asn Ser Lys Arg Asp Ala Glu Ala Val
            100                 105                 110

Gly Pro Glu Ala Phe Ala Asp Glu Asp Leu Asp Glu Arg Glu Val Arg
        115                 120                 125

Gly Ile Gly Lys Phe Leu His Ser Ala Lys Lys Phe Gly Lys Ala Phe
130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
            180                 185                 190

Glu Ile Met Asn Ser Lys Arg Asp Ala Glu Ala Val Gly Pro Glu Ala
        195                 200                 205

Phe Ala Asp Glu Asp Phe Asp Glu Arg Glu Val Arg Gly Ile Gly Lys
    210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
            260                 265                 270

His Ser Ala Lys Lys Phe Gly Lys Ala Phe Val Gly Glu Ile Met Asn
        275                 280                 285

Ser Lys Arg Asp Ala Glu Ala Val Asp Asp Arg Arg Trp Val Glu
    290                 295                 300

<210> SEQ ID NO 5
<211> LENGTH: 17
<212> TYPE: PRT
<213> ORGANISM: Tachypleus gigas
```

<400> SEQUENCE: 5

Lys Trp Cys Phe Arg Val Cys Tyr Arg Gly Ile Cys Tyr Arg Arg Cys
1               5                   10                  15

Arg

<210> SEQ ID NO 6
<211> LENGTH: 17
<212> TYPE: PRT
<213> ORGANISM: Tachypleus gigas

<400> SEQUENCE: 6

Arg Trp Cys Phe Arg Val Cys Tyr Arg Gly Ile Cys Tyr Arg Lys Cys
1               5                   10                  15

Arg

<210> SEQ ID NO 7
<211> LENGTH: 129
<212> TYPE: PRT
<213> ORGANISM: Bufo gargarizans

<400> SEQUENCE: 7

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Val Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Thr Glu Ser Ser Lys Pro Ala Lys Ser
        115                 120                 125

Lys

<210> SEQ ID NO 8
<211> LENGTH: 21
<212> TYPE: PRT
<213> ORGANISM: Bufo gargarizans

<400> SEQUENCE: 8

Thr Arg Ser Ser Arg Ala Gly Leu Gln Phe Pro Val Gly Arg Val His
1               5                   10                  15

Arg Leu Leu Arg Lys
            20

<210> SEQ ID NO 9
<211> LENGTH: 63
<212> TYPE: PRT
<213> ORGANISM: Bombyx mori

<400> SEQUENCE: 9

Met Asn Phe Val Arg Ile Leu Ser Phe Val Phe Ala Leu Val Leu Ala
1               5                   10                  15

```
Leu Gly Ala Val Ser Ala Ala Pro Glu Pro Arg Trp Lys Leu Phe Lys
             20                  25                  30

Lys Ile Glu Lys Val Gly Arg Asn Val Arg Asp Gly Leu Ile Lys Ala
         35                  40                  45

Gly Pro Ala Ile Ala Val Ile Gly Gln Ala Lys Ser Leu Gly Lys
     50                  55                  60

<210> SEQ ID NO 10
<211> LENGTH: 63
<212> TYPE: PRT
<213> ORGANISM: Bombyx mori

<400> SEQUENCE: 10

Met Asn Phe Ala Lys Ile Leu Ser Phe Val Phe Ala Leu Val Leu Ala
 1               5                  10                  15

Leu Ser Met Thr Ser Ala Ala Pro Glu Pro Arg Trp Lys Ile Phe Lys
             20                  25                  30

Lys Ile Glu Lys Met Gly Arg Asn Ile Arg Asp Gly Ile Val Lys Ala
         35                  40                  45

Gly Pro Ala Ile Glu Val Leu Gly Ser Ala Lys Ala Ile Gly Lys
     50                  55                  60

<210> SEQ ID NO 11
<211> LENGTH: 63
<212> TYPE: PRT
<213> ORGANISM: Drosophila melanogaster

<400> SEQUENCE: 11

Met Asn Phe Tyr Lys Ile Phe Val Phe Val Ala Leu Ile Leu Ala Ile
 1               5                  10                  15

Ser Ile Gly Gln Ser Glu Ala Gly Trp Leu Lys Lys Leu Gly Lys Arg
             20                  25                  30

Ile Glu Arg Ile Gly Gln His Thr Arg Asp Ala Thr Ile Gln Gly Leu
         35                  40                  45

Gly Ile Ala Gln Gln Ala Ala Asn Val Ala Ala Thr Ala Arg Gly
     50                  55                  60

<210> SEQ ID NO 12
<211> LENGTH: 31
<212> TYPE: PRT
<213> ORGANISM: Sus scrofa

<400> SEQUENCE: 12

Ser Trp Leu Ser Lys Thr Ala Lys Lys Leu Glu Asn Ser Ala Lys Lys
 1               5                  10                  15

Arg Ile Ser Glu Gly Ile Ala Ile Ala Ile Gln Gly Gly Pro Arg
             20                  25                  30

<210> SEQ ID NO 13
<211> LENGTH: 13
<212> TYPE: PRT
<213> ORGANISM: Bos taurus

<400> SEQUENCE: 13

Ile Leu Pro Trp Lys Trp Pro Trp Trp Pro Trp Arg Arg
 1               5                  10

<210> SEQ ID NO 14
<211> LENGTH: 34
<212> TYPE: PRT
```

<213> ORGANISM: Lactococcus lactis

<400> SEQUENCE: 14

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 15
<211> LENGTH: 20
<212> TYPE: PRT
<213> ORGANISM: Rana catesbeiana

<400> SEQUENCE: 15

Phe Leu Gly Gly Leu Ile Lys Ile Val Pro Ala Met Ile Cys Ala Val
1               5                   10                  15

Thr Lys Lys Cys
            20

<210> SEQ ID NO 16
<211> LENGTH: 25
<212> TYPE: PRT
<213> ORGANISM: Bos taurus

<400> SEQUENCE: 16

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 17
<211> LENGTH: 19
<212> TYPE: PRT
<213> ORGANISM: Sus scrofa
<220> FEATURE:
<221> NAME/KEY: SITE
<222> LOCATION: (19)
<223> OTHER INFORMATION: Xaa at this position can be any amino acid.

<400> SEQUENCE: 17

Arg Gly Gly Arg Leu Cys Tyr Cys Arg Arg Arg Phe Cys Val Cys Val
1               5                   10                  15

Gly Arg Xaa

<210> SEQ ID NO 18
<211> LENGTH: 16
<212> TYPE: PRT
<213> ORGANISM: Sus scrofa

<400> SEQUENCE: 18

Gly Gly Arg Leu Cys Tyr Cys Arg Arg Arg Phe Cys Ile Cys Val Gly
1               5                   10                  15

<210> SEQ ID NO 19
<211> LENGTH: 51
<212> TYPE: PRT
<213> ORGANISM: Homo sapiens

<400> SEQUENCE: 19

Met Lys Phe Phe Val Phe Ala Leu Ile Leu Ala Leu Met Leu Ser Met
1               5                   10                  15

```
Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
        50

<210> SEQ ID NO 20
<211> LENGTH: 38
<212> TYPE: PRT
<213> ORGANISM: Macaca fascicularis

<400> SEQUENCE: 20

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
        35

<210> SEQ ID NO 21
<211> LENGTH: 33
<212> TYPE: PRT
<213> ORGANISM: Phyllomedusa sauvagei

<400> SEQUENCE: 21

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln

<210> SEQ ID NO 22
<211> LENGTH: 34
<212> TYPE: PRT
<213> ORGANISM: Phyllomedusa sauvagei

<400> SEQUENCE: 22

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 23
<211> LENGTH: 30
<212> TYPE: PRT
<213> ORGANISM: Phyllomedusa sauvagei

<400> SEQUENCE: 23

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30

<210> SEQ ID NO 24
<211> LENGTH: 21
<212> TYPE: PRT
<213> ORGANISM: Misgurnus Anguillicaudatus

<400> SEQUENCE: 24
```

```
Arg Gln Arg Val Glu Glu Leu Ser Lys Phe Ser Lys Lys Gly Ala Ala
 1               5                   10                  15

Ala Arg Arg Arg Lys
            20

<210> SEQ ID NO 25
<211> LENGTH: 27
<212> TYPE: PRT
<213> ORGANISM: Apis mellifera

<400> SEQUENCE: 25

Gly Ile Gly Ala Val Leu Lys Val Leu Thr Thr Gly Leu Pro Ala Leu
 1               5                   10                  15

Ile Ser Trp Ile Ser Arg Lys Lys Arg Gln Gln
            20                  25

<210> SEQ ID NO 26
<211> LENGTH: 33
<212> TYPE: PRT
<213> ORGANISM: Pardachirus pavoninus

<400> SEQUENCE: 26

Gly Phe Phe Ala Leu Ile Pro Lys Ile Ile Ser Ser Pro Leu Phe Lys
 1               5                   10                  15

Thr Leu Leu Ser Ala Val Gly Ser Ala Leu Ser Ser Gly Glu Gln
            20                  25                  30

Glu

<210> SEQ ID NO 27
<211> LENGTH: 33
<212> TYPE: PRT
<213> ORGANISM: Pardachirus pavoninus

<400> SEQUENCE: 27

Gly Phe Phe Ala Leu Ile Pro Lys Ile Ile Ser Ser Pro Ile Phe Lys
 1               5                   10                  15

Thr Leu Leu Ser Ala Val Gly Ser Ala Leu Ser Ser Gly Gly Gln
            20                  25                  30

Glu

<210> SEQ ID NO 28
<211> LENGTH: 176
<212> TYPE: PRT
<213> ORGANISM: Bos taurus

<400> SEQUENCE: 28

Met Glu Thr Gln Arg Ala Ser Leu Ser Leu Gly Arg Cys Ser Leu Trp
 1               5                   10                  15

Leu Leu Leu Leu Gly Leu Val Leu Pro Ser Ala Ser Ala Gln Ala Leu
            20                  25                  30

Ser Tyr Arg Glu Ala Val Leu Arg Ala Val Asp Gln Phe Asn Glu Arg
        35                  40                  45

Ser Ser Glu Ala Asn Leu Tyr Arg Leu Leu Glu Leu Asp Pro Thr Pro
    50                  55                  60

Asn Asp Asp Leu Asp Pro Gly Thr Arg Lys Pro Val Ser Phe Arg Val
65                  70                  75                  80

Lys Glu Thr Asp Cys Pro Arg Thr Ser Gln Gln Pro Leu Glu Gln Cys
                85                  90                  95
```

```
Asp Phe Lys Glu Asn Gly Leu Val Lys Gln Cys Val Gly Thr Val Thr
                100                 105                 110

Leu Asp Pro Ser Asn Asp Gln Phe Asp Ile Asn Cys Asn Glu Leu Gln
            115                 120                 125

Ser Val Arg Phe Arg Pro Ile Arg Arg Pro Ile Arg Pro Pro
        130                 135                 140

Phe Tyr Pro Pro Phe Arg Pro Pro Ile Arg Pro Ile Phe Pro Pro
145                 150                 155                 160

Ile Arg Pro Pro Phe Arg Pro Pro Leu Gly Pro Phe Pro Gly Arg Arg
                165                 170                 175

<210> SEQ ID NO 29
<211> LENGTH: 155
<212> TYPE: PRT
<213> ORGANISM: Bos taurus

<400> SEQUENCE: 29

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Gln
        35                  40                  45

Ser Ser Glu Pro Asn Ile Tyr Arg Leu Leu Glu Leu Asp Gln Pro Pro
    50                  55                  60

Gln Asp Asp Glu Asp Pro Asp Ser Pro Lys Arg Val Ser Phe Arg Val
65                  70                  75                  80

Lys Glu Thr Val Cys Ser Arg Thr Thr Gln Gln Pro Pro Glu Gln Cys
                85                  90                  95

Asp Phe Lys Glu Asn Gly Leu Leu Lys Arg Cys Glu Gly Thr Val Thr
                100                 105                 110

Leu Asp Gln Val Arg Gly Asn Phe Asp Ile Thr Cys Asn Asn His Gln
            115                 120                 125

Ser Ile Arg Ile Thr Lys Gln Pro Trp Ala Pro Pro Gln Ala Ala Arg
        130                 135                 140

Leu Cys Arg Ile Val Val Ile Arg Val Cys Arg
145                 150                 155

<210> SEQ ID NO 30
<211> LENGTH: 29
<212> TYPE: PRT
<213> ORGANISM: Ceratitis capitata

<400> SEQUENCE: 30

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
            20                  25

<210> SEQ ID NO 31
<211> LENGTH: 29
<212> TYPE: PRT
<213> ORGANISM: Ceratitis capitata

<400> SEQUENCE: 31

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
            20                  25
```

-continued

```
                20                  25

<210> SEQ ID NO 32
<211> LENGTH: 170
<212> TYPE: PRT
<213> ORGANISM: Homo sapiens

<400> SEQUENCE: 32

Met Lys Thr Gln Arg Asn Gly His Ser Leu Gly Arg Trp Ser Leu Val
 1               5                  10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
        50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
                100                 105                 110

Thr Leu Asn Gln Ala Arg Gly Ser Phe Asp Ile Ser Cys Asp Lys Asp
            115                 120                 125

Asn Lys Arg Phe Ala Leu Leu Gly Asp Phe Phe Arg Lys Ser Lys Glu
        130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 33
<211> LENGTH: 170
<212> TYPE: PRT
<213> ORGANISM: Equus caballus

<400> SEQUENCE: 33

Met Glu Thr Gln Arg Asn Thr Arg Cys Leu Gly Arg Trp Ser Pro Leu
 1               5                  10                  15

Leu Leu Leu Leu Gly Leu Val Ile Pro Pro Ala Thr Thr Gln Ala Leu
                20                  25                  30

Ser Tyr Lys Glu Ala Val Leu Arg Ala Val Asp Gly Leu Asn Gln Arg
            35                  40                  45

Ser Ser Asp Glu Asn Leu Tyr Arg Leu Leu Glu Leu Asp Pro Leu Pro
        50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
                100                 105                 110

Leu Asp Pro Val Lys Asp Tyr Phe Asp Ala Ser Cys Asp Glu Pro Gln
            115                 120                 125

Arg Val Lys Arg Phe His Ser Val Gly Ser Leu Ile Gln Arg His Gln
        130                 135                 140

Gln Met Ile Arg Asp Lys Ser Glu Ala Thr Arg His Gly Ile Arg Ile
```

```
                145                 150                 155                 160
Ile Thr Arg Pro Lys Leu Leu Leu Ala Ser
                165                 170

<210> SEQ ID NO 34
<211> LENGTH: 159
<212> TYPE: PRT
<213> ORGANISM: Bos taurus

<400> SEQUENCE: 34

Met Glu Thr Gln Arg Ala Ser Leu Ser Leu Gly Arg Trp Ser Leu Trp
  1               5                  10                  15

Leu Leu Leu Leu Gly Leu Ala Leu Pro Ser Ala Ser Ala Gln Ala Leu
                 20                  25                  30

Ser Tyr Arg Glu Ala Val Leu Arg Ala Val Asp Gln Leu Asn Glu Lys
             35                  40                  45

Ser Ser Glu Ala Asn Leu Tyr Arg Leu Leu Glu Leu Asp Pro Pro Pro
         50                  55                  60

Lys Glu Asp Asp Glu Asn Pro Asn Ile Pro Lys Pro Val Ser Phe Arg
 65                  70                  75                  80

Val Lys Glu Thr Val Cys Pro Arg Thr Ser Gln Gln Ser Pro Glu Gln
                 85                  90                  95

Cys Asp Phe Lys Glu Asn Gly Leu Leu Lys Glu Cys Val Gly Thr Val
            100                 105                 110

Thr Leu Asp Gln Val Gly Ser Asn Phe Asp Ile Thr Cys Ala Val Pro
        115                 120                 125

Gln Ser Val Gly Gly Leu Arg Ser Leu Gly Arg Lys Ile Leu Arg Ala
    130                 135                 140

Trp Lys Lys Tyr Gly Pro Ile Ile Val Pro Ile Ile Arg Ile Gly
145                 150                 155

<210> SEQ ID NO 35
<211> LENGTH: 156
<212> TYPE: PRT
<213> ORGANISM: Equus asinus

<400> SEQUENCE: 35

Met Glu Thr Gln Arg Asn Thr Arg Cys Leu Gly Arg Trp Ser Pro Leu
  1               5                  10                  15

Leu Leu Leu Leu Gly Leu Val Ile Pro Pro Ala Thr Thr Gln Ala Leu
                 20                  25                  30

Ser Tyr Lys Glu Ala Val Leu Arg Ala Val Asp Gly Leu Asn Gln Arg
             35                  40                  45

Ser Ser Asp Glu Asn Leu Tyr Arg Leu Leu Glu Leu Asp Pro Leu Pro
         50                  55                  60

Lys Gly Asp Lys Asp Ser Asp Thr Pro Lys Pro Val Ser Phe Met Val
 65                  70                  75                  80

Lys Glu Thr Val Cys Pro Arg Ile Met Lys Gln Thr Pro Glu Gln Cys
                 85                  90                  95

Asp Phe Lys Glu Asn Gly Leu Val Lys Gln Cys Val Gly Thr Val Ile
            100                 105                 110

Leu Gly Pro Val Lys Asp His Phe Asp Val Ser Cys Gly Glu Pro Gln
        115                 120                 125

Arg Val Lys Arg Phe Gly Arg Leu Ala Lys Ser Phe Leu Arg Met Arg
    130                 135                 140

Ile Leu Leu Pro Arg Arg Lys Ile Leu Leu Ala Ser
145                 150                 155
```

<210> SEQ ID NO 36
<211> LENGTH: 160
<212> TYPE: PRT
<213> ORGANISM: Ovis aries

<400> SEQUENCE: 36

Met Glu Thr Gln Arg Ala Ser Leu Ser Leu Gly Arg Cys Ser Leu Trp
1               5                   10                  15

Leu Leu Leu Leu Gly Leu Ala Leu Pro Ser Ala Ser Ala Gln Val Leu
            20                  25                  30

Ser Tyr Arg Glu Ala Val Leu Arg Ala Ala Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Gln Asp Asp Glu Asn Ser Asn Ile Pro Lys Pro Val Ser Phe Arg
65                  70                  75                  80

Val Lys Glu Thr Val Cys Pro Arg Thr Ser Gln Gln Pro Ala Glu Gln
                85                  90                  95

Cys Asp Phe Lys Glu Asn Gly Leu Leu Lys Glu Cys Val Gly Thr Val
            100                 105                 110

Thr Leu Asp Gln Val Arg Asn Asn Phe Asp Ile Thr Cys Ala Glu Pro
        115                 120                 125

Gln Ser Val Arg Gly Leu Arg Arg Leu Gly Arg Lys Ile Ala His Gly
    130                 135                 140

Val Lys Lys Tyr Gly Pro Thr Val Leu Arg Ile Ile Arg Ile Ala Gly
145                 150                 155                 160

<210> SEQ ID NO 37
<211> LENGTH: 12
<212> TYPE: PRT
<213> ORGANISM: Bos taurus

<400> SEQUENCE: 37

Arg Leu Cys Arg Ile Val Val Ile Arg Val Cys Arg
1               5                   10

<210> SEQ ID NO 38
<211> LENGTH: 30
<212> TYPE: PRT
<213> ORGANISM: Homo sapiens

<400> SEQUENCE: 38

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 39
<211> LENGTH: 29
<212> TYPE: PRT
<213> ORGANISM: Homo sapiens

<400> SEQUENCE: 39

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

```
<210> SEQ ID NO 40
<211> LENGTH: 30
<212> TYPE: PRT
<213> ORGANISM: Homo sapiens

<400> SEQUENCE: 40

Asp Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
             20                  25                  30

<210> SEQ ID NO 41
<211> LENGTH: 33
<212> TYPE: PRT
<213> ORGANISM: Homo sapiens

<400> SEQUENCE: 41

Val Cys Ser Cys Arg Leu Val Phe Cys Arg Arg Thr Glu Leu Arg Val
 1               5                  10                  15

Gly Asn Cys Leu Ile Gly Gly Val Ser Phe Thr Tyr Cys Cys Thr Arg
             20                  25                  30

Val

<210> SEQ ID NO 42
<211> LENGTH: 33
<212> TYPE: PRT
<213> ORGANISM: Oryctolagus cuniculus

<400> SEQUENCE: 42

Val Val Cys Ala Cys Arg Arg Ala Leu Cys Leu Pro Arg Glu Arg Arg
 1               5                  10                  15

Ala Gly Phe Cys Arg Ile Arg Gly Arg Ile His Pro Leu Cys Cys Arg
             20                  25                  30

Arg

<210> SEQ ID NO 43
<211> LENGTH: 33
<212> TYPE: PRT
<213> ORGANISM: Oryctolagus cuniculus

<400> SEQUENCE: 43

Val Val Cys Ala Cys Arg Arg Ala Leu Cys Leu Pro Leu Glu Arg Arg
 1               5                  10                  15

Ala Gly Phe Cys Arg Ile Arg Gly Arg Ile His Pro Leu Cys Cys Arg
             20                  25                  30

Arg

<210> SEQ ID NO 44
<211> LENGTH: 34
<212> TYPE: PRT
<213> ORGANISM: Oryctolagus cuniculus

<400> SEQUENCE: 44

Gly Ile Cys Ala Cys Arg Arg Arg Phe Cys Pro Asn Ser Glu Arg Phe
 1               5                  10                  15

Ser Gly Tyr Cys Arg Val Asn Gly Ala Arg Tyr Val Arg Cys Cys Ser
             20                  25                  30

Arg Arg
```

```
<210> SEQ ID NO 45
<211> LENGTH: 34
<212> TYPE: PRT
<213> ORGANISM: Oryctolagus cuniculus

<400> SEQUENCE: 45

Gly Arg Cys Val Cys Arg Lys Gln Leu Leu Cys Ser Tyr Arg Glu Arg
 1               5                  10                  15

Arg Ile Gly Asp Cys Lys Ile Arg Gly Val Arg Phe Pro Phe Cys Cys
                20                  25                  30

Pro Arg

<210> SEQ ID NO 46
<211> LENGTH: 34
<212> TYPE: PRT
<213> ORGANISM: Oryctolagus cuniculus

<400> SEQUENCE: 46

Val Ser Cys Thr Cys Arg Arg Phe Ser Cys Gly Phe Gly Glu Arg Ala
 1               5                  10                  15

Ser Gly Ser Cys Thr Val Asn Gly Gly Val Arg His Thr Leu Cys Cys
                20                  25                  30

Arg Arg

<210> SEQ ID NO 47
<211> LENGTH: 33
<212> TYPE: PRT
<213> ORGANISM: Oryctolagus cuniculus

<400> SEQUENCE: 47

Val Phe Cys Thr Cys Arg Gly Phe Leu Cys Gly Ser Gly Glu Arg Ala
 1               5                  10                  15

Ser Gly Ser Cys Thr Ile Asn Gly Val Arg His Thr Leu Cys Cys Arg
                20                  25                  30

Arg

<210> SEQ ID NO 48
<211> LENGTH: 32
<212> TYPE: PRT
<213> ORGANISM: Rattus norvegicus

<400> SEQUENCE: 48

Val Thr Cys Tyr Cys Arg Arg Thr Arg Cys Gly Phe Arg Glu Arg Leu
 1               5                  10                  15

Ser Gly Ala Cys Gly Tyr Arg Gly Arg Ile Tyr Arg Leu Cys Cys Arg
                20                  25                  30

<210> SEQ ID NO 49
<211> LENGTH: 30
<212> TYPE: PRT
<213> ORGANISM: Rattus norvegicus

<400> SEQUENCE: 49

Cys Ser Cys Arg Tyr Ser Ser Cys Arg Phe Gly Glu Arg Leu Leu Ser
 1               5                  10                  15

Gly Ala Cys Arg Leu Asn Gly Arg Ile Tyr Arg Leu Cys Cys
                20                  25                  30

<210> SEQ ID NO 50
<211> LENGTH: 31
<212> TYPE: PRT
```

<213> ORGANISM: Rattus norvegicus

<400> SEQUENCE: 50

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 51
<211> LENGTH: 31
<212> TYPE: PRT
<213> ORGANISM: Guinea pig cytomegalovirus

<400> SEQUENCE: 51

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 52
<211> LENGTH: 67
<212> TYPE: PRT
<213> ORGANISM: Homo sapiens

<400> SEQUENCE: 52

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 53
<211> LENGTH: 18
<212> TYPE: PRT
<213> ORGANISM: Macaca mulatta

<400> SEQUENCE: 53

Arg Cys Ile Cys Thr Arg Gly Phe Cys Arg Cys Leu Cys Arg Arg Gly
1               5                   10                  15

Val Cys

<210> SEQ ID NO 54
<211> LENGTH: 78
<212> TYPE: PRT
<213> ORGANISM: Helianthus annuus

<400> SEQUENCE: 54

Met Lys Ser Ser Met Lys Met Phe Ala Ala Leu Leu Val Val Met
1               5                   10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
        35                  40                  45

Thr Asn Cys Ala Asn Val Cys His Ser Glu Arg Phe Ser Gly Gly Lys
    50                  55                  60

```
Cys Arg Gly Phe Arg Arg Arg Cys Phe Cys Thr Thr His Cys
 65                  70                  75
```

<210> SEQ ID NO 55
<211> LENGTH: 78
<212> TYPE: PRT
<213> ORGANISM: Helianthus annuus

<400> SEQUENCE: 55

```
Met Lys Ser Ser Met Lys Met Phe Ala Ala Leu Leu Leu Val Val Met
 1               5                  10                  15

Cys Leu Leu Ala Asn Glu Met Gly Gly Pro Leu Val Val Glu Ala Arg
             20                  25                  30

Thr Cys Glu Ser Gln Ser His Lys Phe Lys Gly Thr Cys Leu Ser Asp
         35                  40                  45

Thr Asn Cys Ala Asn Val Cys His Ser Glu Arg Phe Ser Gly Gly Lys
     50                  55                  60

Cys Arg Gly Phe Arg Arg Arg Cys Phe Cys Thr Thr His Cys
 65                  70                  75
```

<210> SEQ ID NO 56
<211> LENGTH: 30
<212> TYPE: PRT
<213> ORGANISM: Macaca mulatta

<400> SEQUENCE: 56

```
Ala Cys Tyr Cys Arg Ile Pro Ala Cys Leu Ala Gly Glu Arg Arg Tyr
 1               5                  10                  15

Gly Thr Cys Phe Tyr Met Gly Arg Val Trp Ala Phe Cys Cys
             20                  25                  30
```

<210> SEQ ID NO 57
<211> LENGTH: 37
<212> TYPE: PRT
<213> ORGANISM: Androctonus Australis Hector

<400> SEQUENCE: 57

```
Gly Phe Gly Cys Pro Phe Asn Gln Gly Ala Cys His Arg His Cys Arg
 1               5                  10                  15

Ser Ile Arg Arg Arg Gly Gly Tyr Cys Ala Gly Leu Phe Lys Gln Thr
             20                  25                  30

Cys Thr Cys Tyr Arg
         35
```

<210> SEQ ID NO 58
<211> LENGTH: 38
<212> TYPE: PRT
<213> ORGANISM: Mytilus galloprovincialis
<220> FEATURE:
<221> NAME/KEY: SITE
<222> LOCATION: (28)
<223> OTHER INFORMATION: Xaa at this position can be any amino acid.

<400> SEQUENCE: 58

```
Gly Phe Gly Cys Pro Asn Asn Tyr Gln Cys His Arg His Cys Lys Ser
 1               5                  10                  15

Ile Pro Gly Arg Cys Gly Gly Tyr Cys Gly Gly Xaa His Arg Leu Arg
             20                  25                  30

Cys Thr Cys Tyr Arg Cys
         35
```

-continued

```
<210> SEQ ID NO 59
<211> LENGTH: 54
<212> TYPE: PRT
<213> ORGANISM: Heuchera sanguinea

<400> SEQUENCE: 59

Asp Gly Val Lys Leu Cys Asp Val Pro Ser Gly Thr Trp Ser Gly His
 1               5                  10                  15

Cys Gly Ser Ser Lys Cys Ser Gln Gln Cys Lys Asp Arg Glu His
                20                  25                  30

Phe Ala Tyr Gly Gly Ala Cys His Tyr Gln Phe Pro Ser Val Lys Cys
            35                  40                  45

Phe Cys Lys Arg Gln Cys
        50

<210> SEQ ID NO 60
<211> LENGTH: 49
<212> TYPE: PRT
<213> ORGANISM: Clitoria ternatea

<400> SEQUENCE: 60

Asn Leu Cys Glu Arg Ala Ser Leu Thr Trp Thr Gly Asn Cys Gly Asn
 1               5                  10                  15

Thr Gly His Cys Asp Thr Gln Cys Arg Asn Trp Glu Ser Ala Lys His
                20                  25                  30

Gly Ala Cys His Lys Arg Gly Asn Trp Lys Cys Phe Cys Tyr Phe Asn
            35                  40                  45

Cys

<210> SEQ ID NO 61
<211> LENGTH: 91
<212> TYPE: PRT
<213> ORGANISM: Mus musculus

<400> SEQUENCE: 61

Met Lys Lys Leu Val Leu Leu Phe Ala Leu Val Leu Leu Ala Phe Gln
 1               5                  10                  15

Val Gln Ala Asp Ser Ile Gln Asn Thr Asp Glu Glu Thr Lys Thr Glu
                20                  25                  30

Glu Gln Pro Gly Glu Lys Asp Gln Ala Val Ser Val Ser Phe Gly Asp
            35                  40                  45

Pro Gln Gly Ser Ala Leu Gln Asp Ala Ala Leu Gly Trp Gly Arg Arg
        50                  55                  60

Cys Pro Gln Cys Pro Arg Cys Pro Ser Cys Pro Ser Cys Pro Arg Cys
65                  70                  75                  80

Pro Arg Cys Pro Arg Cys Lys Cys Asn Pro Lys
                85                  90

<210> SEQ ID NO 62
<211> LENGTH: 40
<212> TYPE: PRT
<213> ORGANISM: Bos taurus

<400> SEQUENCE: 62

Gln Gly Val Arg Asn Phe Val Thr Cys Arg Ile Asn Arg Gly Phe Cys
 1               5                  10                  15

Val Pro Ile Arg Cys Pro Gly His Arg Arg Gln Ile Gly Thr Cys Leu
                20                  25                  30
```

```
Gly Pro Gln Ile Lys Cys Cys Arg
        35                  40
```

<210> SEQ ID NO 63
<211> LENGTH: 40
<212> TYPE: PRT
<213> ORGANISM: Bos taurus

<400> SEQUENCE: 63

```
Gln Gly Val Arg Asn Phe Val Thr Cys Arg Ile Asn Arg Gly Phe Cys
 1               5                  10                  15

Val Pro Ile Arg Cys Pro Gly His Arg Gln Ile Gly Thr Cys Leu
            20                  25                  30

Gly Pro Arg Ile Lys Cys Cys Arg
        35                  40
```

<210> SEQ ID NO 64
<211> LENGTH: 42
<212> TYPE: PRT
<213> ORGANISM: Bos taurus

<400> SEQUENCE: 64

```
Gln Gly Val Arg Asn His Val Thr Cys Arg Ile Tyr Gly Gly Phe Cys
 1               5                  10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40
```

<210> SEQ ID NO 65
<211> LENGTH: 40
<212> TYPE: PRT
<213> ORGANISM: Bos taurus

<400> SEQUENCE: 65

```
Gln Val Val Arg Asn Pro Gln Ser Cys Arg Trp Asn Met Gly Val Cys
 1               5                  10                  15

Ile Pro Ile Ser Cys Pro Gly Asn Met Arg Gln Ile Gly Thr Cys Phe
            20                  25                  30

Gly Pro Arg Val Pro Cys Cys Arg
        35                  40
```

<210> SEQ ID NO 66
<211> LENGTH: 41
<212> TYPE: PRT
<213> ORGANISM: Bos taurus

<400> SEQUENCE: 66

```
Gln Arg Val Arg Asn Pro Gln Ser Cys Arg Trp Asn Met Gly Val Cys
 1               5                  10                  15

Ile Pro Phe Leu Cys Arg Val Gly Met Arg Gln Ile Gly Thr Cys Phe
            20                  25                  30

Gly Pro Arg Val Pro Cys Cys Arg Arg
        35                  40
```

<210> SEQ ID NO 67
<211> LENGTH: 42
<212> TYPE: PRT
<213> ORGANISM: Bos taurus

<400> SEQUENCE: 67

```
Gln Gly Val Arg Asn His Val Thr Cys Arg Ile Asn Arg Gly Phe Cys
 1               5                  10                  15

Val Pro Ile Arg Cys Pro Gly Arg Thr Arg Gln Ile Gly Thr Cys Phe
                20                  25                  30

Gly Pro Arg Ile Lys Cys Cys Arg Ser Trp
            35                  40
```

<210> SEQ ID NO 68
<211> LENGTH: 40
<212> TYPE: PRT
<213> ORGANISM: Bos taurus

<400> SEQUENCE: 68

```
Gln Gly Val Arg Ser Tyr Leu Ser Cys Trp Gly Asn Arg Gly Ile Cys
 1               5                  10                  15

Leu Leu Asn Arg Cys Pro Gly Arg Met Arg Gln Ile Gly Thr Cys Leu
                20                  25                  30

Ala Pro Arg Val Lys Cys Cys Arg
            35                  40
```

<210> SEQ ID NO 69
<211> LENGTH: 42
<212> TYPE: PRT
<213> ORGANISM: Bos taurus

<400> SEQUENCE: 69

```
Ser Gly Ile Ser Gly Pro Leu Ser Cys Gly Arg Asn Gly Gly Val Cys
 1               5                  10                  15

Ile Pro Ile Arg Cys Pro Val Pro Met Arg Gln Ile Gly Thr Cys Phe
                20                  25                  30

Gly Arg Pro Val Lys Cys Cys Arg Ser Trp
            35                  40
```

<210> SEQ ID NO 70
<211> LENGTH: 38
<212> TYPE: PRT
<213> ORGANISM: Bos taurus

<400> SEQUENCE: 70

```
Asp Phe Ala Ser Cys His Thr Asn Gly Gly Ile Cys Leu Pro Asn Arg
 1               5                  10                  15

Cys Pro Gly His Met Ile Gln Ile Gly Ile Cys Phe Arg Pro Arg Val
                20                  25                  30

Lys Cys Cys Arg Ser Trp
            35
```

<210> SEQ ID NO 71
<211> LENGTH: 74
<212> TYPE: PRT
<213> ORGANISM: Zophobas atratus

<400> SEQUENCE: 71

```
Ser Leu Gln Gly Gly Ala Pro Asn Phe Pro Gln Pro Ser Gln Gln Asn
 1               5                  10                  15

Gly Gly Trp Gln Val Ser Pro Asp Leu Gly Arg Asp Asp Lys Gly Asn
                20                  25                  30

Thr Arg Gly Gln Ile Glu Ile Gln Asn Lys Gly Lys Asp His Asp Phe
            35                  40                  45

Asn Ala Gly Trp Gly Lys Val Ile Arg Gly Pro Asn Lys Ala Lys Pro
        50                  55                  60
```

```
Thr Trp His Val Gly Gly Thr Tyr Arg Arg
 65                  70
```

<210> SEQ ID NO 72
<211> LENGTH: 67
<212> TYPE: PRT
<213> ORGANISM: Homo sapiens

<400> SEQUENCE: 72

```
Met Arg Ile His Tyr Leu Leu Phe Ala Leu Leu Phe Leu Phe Leu Val
 1               5                  10                  15

Pro Val Pro Gly His Gly Gly Ile Ile Asn Thr Leu Gln Lys Tyr Tyr
             20                  25                  30

Cys Arg Val Arg Gly Gly Arg Cys Ala Val Leu Ser Cys Leu Pro Lys
         35                  40                  45

Glu Glu Gln Ile Gly Lys Cys Ser Thr Arg Gly Arg Lys Cys Cys Arg
     50                  55                  60

Arg Lys Lys
 65
```

<210> SEQ ID NO 73
<211> LENGTH: 40
<212> TYPE: PRT
<213> ORGANISM: Aedes aegypti

<400> SEQUENCE: 73

```
Ala Thr Cys Asp Leu Leu Ser Gly Phe Gly Val Gly Asp Ser Ala Cys
 1               5                  10                  15

Ala Ala His Cys Ile Ala Arg Gly Asn Arg Gly Gly Tyr Cys Asn Ser
             20                  25                  30

Lys Lys Val Cys Val Cys Arg Asn
         35                  40
```

<210> SEQ ID NO 74
<211> LENGTH: 35
<212> TYPE: PRT
<213> ORGANISM: Mytilus edulis
<220> FEATURE:
<221> NAME/KEY: SITE
<222> LOCATION: (28)
<223> OTHER INFORMATION: Xaa at this position can be any amino acid.

<400> SEQUENCE: 74

```
Gly Phe Gly Cys Pro Asn Asp Tyr Pro Cys His Arg His Cys Lys Ser
 1               5                  10                  15

Ile Pro Gly Arg Tyr Gly Gly Tyr Cys Gly Gly Xaa His Arg Leu Arg
             20                  25                  30

Cys Thr Cys
         35
```

<210> SEQ ID NO 75
<211> LENGTH: 40
<212> TYPE: PRT
<213> ORGANISM: Sarcophaga peregrina

<400> SEQUENCE: 75

```
Ala Thr Cys Asp Leu Leu Ser Gly Ile Gly Val Gln His Ser Ala Cys
 1               5                  10                  15

Ala Leu His Cys Val Phe Arg Gly Asn Arg Gly Gly Tyr Cys Thr Gly
             20                  25                  30
```

```
Lys Gly Ile Cys Val Cys Arg Asn
        35              40

<210> SEQ ID NO 76
<211> LENGTH: 95
<212> TYPE: PRT
<213> ORGANISM: Oryctolagus cuniculus

<400> SEQUENCE: 76

Met Arg Thr Leu Ala Leu Leu Ala Ala Ile Leu Leu Val Ala Leu Gln
 1               5                  10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
        35                  40                  45

His Glu Ser Ser Ala Leu Glu Ala Leu Gly Val Lys Ala Gly Val Val
    50                  55                  60

Cys Ala Cys Arg Arg Ala Leu Cys Leu Pro Arg Glu Arg Arg Ala Gly
 65                  70                  75                  80

Phe Cys Arg Ile Arg Gly Arg Ile His Pro Leu Cys Cys Arg Arg
                85                  90                  95

<210> SEQ ID NO 77
<211> LENGTH: 92
<212> TYPE: PRT
<213> ORGANISM: Mus musculus

<400> SEQUENCE: 77

Met Lys Pro Leu Val Leu Leu Ser Ala Leu Val Leu Leu Ser Phe Gln
 1               5                  10                  15

Val Gln Ala Asp Pro Ile Gln Asn Thr Asp Glu Glu Thr Lys Thr Glu
            20                  25                  30

Glu Gln Ser Gly Glu Glu Asp Gln Ala Val Ser Val Ser Phe Gly Asp
        35                  40                  45

Arg Glu Gly Ala Ser Leu Gln Glu Glu Ser Leu Arg Asp Leu Val Cys
    50                  55                  60

Tyr Cys Arg Thr Arg Gly Cys Lys Arg Arg Glu Arg Met Asn Gly Thr
 65                  70                  75                  80

Cys Arg Lys Gly His Leu Met Tyr Thr Leu Cys Cys
                85                  90

<210> SEQ ID NO 78
<211> LENGTH: 93
<212> TYPE: PRT
<213> ORGANISM: Mus musculus

<400> SEQUENCE: 78

Met Lys Thr Phe Val Leu Leu Ser Ala Leu Val Leu Leu Ala Phe Gln
 1               5                  10                  15

Val Gln Ala Asp Pro Ile His Lys Thr Asp Glu Glu Thr Asn Thr Glu
            20                  25                  30

Glu Gln Pro Gly Glu Glu Asp Gln Ala Val Ser Ile Ser Phe Gly Gly
        35                  40                  45

Gln Glu Gly Ser Ala Leu His Glu Glu Leu Ser Lys Lys Leu Ile Cys
    50                  55                  60

Tyr Cys Arg Ile Arg Gly Cys Lys Arg Arg Glu Arg Val Phe Gly Thr
 65                  70                  75                  80

Cys Arg Asn Leu Phe Leu Thr Phe Val Phe Cys Cys Ser
```

<210> SEQ ID NO 79
<211> LENGTH: 35
<212> TYPE: PRT
<213> ORGANISM: Mus musculus

<400> SEQUENCE: 79

Leu Arg Asp Leu Val Cys Tyr Cys Arg Ala Arg Gly Cys Lys Gly Arg
 1               5                  10                  15

Glu Arg Met Asn Gly Thr Cys Arg Lys Gly His Leu Leu Tyr Met Leu
            20                  25                  30

Cys Cys Arg
         35

<210> SEQ ID NO 80
<211> LENGTH: 43
<212> TYPE: PRT
<213> ORGANISM: Pyrrhocoris apterus

<400> SEQUENCE: 80

Ala Thr Cys Asp Ile Leu Ser Phe Gln Ser Gln Trp Val Thr Pro Asn
 1               5                  10                  15

His Ala Gly Cys Ala Leu His Cys Val Ile Lys Gly Tyr Lys Gly Gly
            20                  25                  30

Gln Cys Lys Ile Thr Val Cys His Cys Arg Arg
         35                  40

<210> SEQ ID NO 81
<211> LENGTH: 32
<212> TYPE: PRT
<213> ORGANISM: Rattus norvegicus

<400> SEQUENCE: 81

Val Thr Cys Tyr Cys Arg Ser Thr Arg Cys Gly Phe Arg Glu Arg Leu
 1               5                  10                  15

Ser Gly Ala Cys Gly Tyr Arg Gly Arg Ile Tyr Arg Leu Cys Cys Arg
            20                  25                  30

<210> SEQ ID NO 82
<211> LENGTH: 31
<212> TYPE: PRT
<213> ORGANISM: Rattus norvegicus

<400> SEQUENCE: 82

Val Thr Cys Ser Cys Arg Thr Ser Ser Cys Arg Phe Gly Glu Arg Leu
 1               5                  10                  15

Ser Gly Ala Cys Arg Leu Asn Gly Arg Ile Tyr Arg Leu Cys Cys
            20                  25                  30

<210> SEQ ID NO 83
<211> LENGTH: 34
<212> TYPE: PRT
<213> ORGANISM: Oryctolagus cuniculus

<400> SEQUENCE: 83

Gly Ile Cys Ala Cys Arg Arg Arg Phe Cys Leu Asn Phe Glu Gln Phe
 1               5                  10                  15

Ser Gly Tyr Cys Arg Val Asn Gly Ala Arg Tyr Val Arg Cys Cys Ser
            20                  25                  30

Arg Arg

<210> SEQ ID NO 84
<211> LENGTH: 64
<212> TYPE: PRT
<213> ORGANISM: Pan troglodytes

<400> SEQUENCE: 84

Met Arg Val Leu Tyr Leu Leu Phe Ser Phe Leu Phe Ile Phe Leu Met
1               5                   10                  15

Pro Leu Pro Gly Val Phe Gly Gly Ile Ser Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 85
<211> LENGTH: 64
<212> TYPE: PRT
<213> ORGANISM: Homo sapiens

<400> SEQUENCE: 85

Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 86
<211> LENGTH: 68
<212> TYPE: PRT
<213> ORGANISM: Homo sapiens

<400> SEQUENCE: 86

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 87
<211> LENGTH: 64
<212> TYPE: PRT
<213> ORGANISM: Capra hircus

<400> SEQUENCE: 87

Met Arg Leu His His Leu Leu Leu Val Leu Phe Phe Leu Val Leu Ser
1               5                   10                  15

Ala Gly Ser Gly Phe Thr Gln Gly Ile Arg Ser Arg Arg Ser Cys His
            20                  25                  30

Arg Asn Lys Gly Val Cys Ala Leu Thr Arg Cys Pro Arg Asn Met Arg

```
                35                  40                  45
Gln Ile Gly Thr Cys Phe Gly Pro Pro Val Lys Cys Cys Arg Lys Lys
        50                  55                  60
```

<210> SEQ ID NO 88
<211> LENGTH: 64
<212> TYPE: PRT
<213> ORGANISM: Capra hircus

<400> SEQUENCE: 88

```
Met Arg Leu His His Leu Leu Leu Ala Leu Phe Phe Leu Val Leu Ser
  1               5                  10                  15

Ala Gly Ser Gly Phe Thr Gln Gly Ile Ile Asn His Arg Ser Cys Tyr
                20                  25                  30

Arg Asn Lys Gly Val Cys Ala Pro Ala Arg Cys Pro Arg Asn Met Arg
            35                  40                  45

Gln Ile Gly Thr Cys His Gly Pro Pro Val Lys Cys Cys Arg Lys Lys
        50                  55                  60
```

<210> SEQ ID NO 89
<211> LENGTH: 96
<212> TYPE: PRT
<213> ORGANISM: Macaca mulatta

<400> SEQUENCE: 89

```
Met Arg Thr Leu Val Ile Leu Ala Ala Ile Leu Leu Val Ala Leu Gln
  1               5                  10                  15

Ala Gln Ala Glu Pro Leu Gln Ala Arg Thr Asp Glu Ala Thr Ala Ala
                20                  25                  30

Gln Glu Gln Ile Pro Thr Asp Asn Pro Glu Val Val Val Ser Leu Ala
            35                  40                  45

Trp Asp Glu Ser Leu Ala Pro Lys Asp Ser Val Pro Gly Leu Arg Lys
        50                  55                  60

Asn Met Ala Cys Tyr Cys Arg Ile Pro Ala Cys Leu Ala Gly Glu Arg
 65                  70                  75                  80

Arg Tyr Gly Thr Cys Phe Tyr Arg Arg Arg Val Trp Ala Phe Cys Cys
                85                  90                  95
```

<210> SEQ ID NO 90
<211> LENGTH: 96
<212> TYPE: PRT
<213> ORGANISM: Macaca mulatta

<400> SEQUENCE: 90

```
Met Arg Thr Leu Val Ile Leu Ala Ala Ile Leu Leu Val Ala Leu Gln
  1               5                  10                  15

Ala Gln Ala Glu Pro Leu Gln Ala Arg Thr Asp Glu Ala Thr Ala Ala
                20                  25                  30

Gln Glu Gln Ile Pro Thr Asp Asn Pro Glu Val Val Val Ser Leu Ala
            35                  40                  45

Trp Asp Glu Ser Leu Ala Pro Lys Asp Ser Val Pro Gly Leu Arg Lys
        50                  55                  60

Asn Met Ala Cys Tyr Cys Arg Ile Pro Ala Cys Leu Ala Gly Glu Arg
 65                  70                  75                  80

Arg Tyr Gly Thr Cys Phe Tyr Leu Gly Arg Val Trp Ala Phe Cys Cys
                85                  90                  95
```

<210> SEQ ID NO 91

```
<211> LENGTH: 33
<212> TYPE: PRT
<213> ORGANISM: Mesocricetus auratus

<400> SEQUENCE: 91

Val Thr Cys Phe Cys Arg Arg Arg Gly Cys Ala Ser Arg Glu Arg His
 1               5                  10                  15

Ile Gly Tyr Cys Arg Phe Gly Asn Thr Ile Tyr Arg Leu Cys Cys Arg
            20                  25                  30

Arg

<210> SEQ ID NO 92
<211> LENGTH: 31
<212> TYPE: PRT
<213> ORGANISM: Mesocricetus auratus

<400> SEQUENCE: 92

Cys Phe Cys Lys Arg Pro Val Cys Asp Ser Gly Glu Thr Gln Ile Gly
 1               5                  10                  15

Tyr Cys Arg Leu Gly Asn Thr Phe Tyr Arg Leu Cys Cys Arg Gln
            20                  25                  30

<210> SEQ ID NO 93
<211> LENGTH: 39
<212> TYPE: PRT
<213> ORGANISM: Gallus gallus

<400> SEQUENCE: 93

Gly Arg Lys Ser Asp Cys Phe Arg Lys Asn Gly Phe Cys Ala Phe Leu
 1               5                  10                  15

Lys Cys Pro Tyr Leu Thr Leu Ile Ser Gly Lys Cys Ser Arg Phe His
            20                  25                  30

Leu Cys Cys Lys Arg Ile Trp
        35

<210> SEQ ID NO 94
<211> LENGTH: 43
<212> TYPE: PRT
<213> ORGANISM: Allomyrina dichotoma

<400> SEQUENCE: 94

Val Thr Cys Asp Leu Leu Ser Phe Glu Ala Lys Gly Phe Ala Ala Asn
 1               5                  10                  15

His Ser Leu Cys Ala Ala His Cys Leu Ala Ile Gly Arg Arg Gly Gly
            20                  25                  30

Ser Cys Glu Arg Gly Val Cys Ile Cys Arg Arg
        35                  40

<210> SEQ ID NO 95
<211> LENGTH: 31
<212> TYPE: PRT
<213> ORGANISM: Cavia porcellus

<400> SEQUENCE: 95

Arg Arg Cys Ile Cys Thr Thr Arg Thr Cys Arg Phe Pro Tyr Arg Arg
 1               5                  10                  15

Leu Gly Thr Cys Ile Phe Gln Asn Arg Val Tyr Thr Phe Cys Cys
            20                  25                  30

<210> SEQ ID NO 96
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (1)
<223> OTHER INFORMATION: Represents conservatively or nonconservatively
      substituted amino acid.
<220> FEATURE:
<221> NAME/KEY: UNSURE
<222> LOCATION: (3)
<223> OTHER INFORMATION: Represents conservatively or nonconservatively
      substituted amino acid.
<220> FEATURE:
<221> NAME/KEY: UNSURE
<222> LOCATION: (6)
<223> OTHER INFORMATION: Represents conservatively or nonconservatively
      substituted amino acid.
<220> FEATURE:
<221> NAME/KEY: UNSURE
<222> LOCATION: (8)
<223> OTHER INFORMATION: Represents conservatively or nonconservatively
      substituted amino acid.
<220> FEATURE:
<221> NAME/KEY: UNSURE
<222> LOCATION: (11)
<223> OTHER INFORMATION: Represents conservatively or nonconservatively
      substituted amino acid.
<220> FEATURE:
<221> NAME/KEY: UNSURE
<222> LOCATION: (13)
<223> OTHER INFORMATION: Represents conservatively or nonconservatively
      substituted amino acid.
<220> FEATURE:
<221> NAME/KEY: UNSURE
<222> LOCATION: (15)
<223> OTHER INFORMATION: Represents conservatively or nonconservatively
      substituted amino acid.
<220> FEATURE:
<221> NAME/KEY: UNSURE
<222> LOCATION: (18)
<223> OTHER INFORMATION: Represents conservatively or nonconservatively
      substituted amino acid.
<220> FEATURE:
<221> NAME/KEY: SITE
<222> LOCATION: (1)
<223> OTHER INFORMATION: Xaa at this position can be any amino acid.
<220> FEATURE:
<221> NAME/KEY: SITE
<222> LOCATION: (18)
<223> OTHER INFORMATION: Xaa at this position can be any amino acid.

<400> SEQUENCE: 96

Xaa Cys Asn Cys Arg Asn Cys Asn Glu Arg Asn Cys Asn Gly Asn Cys
 1               5                  10                  15

Cys Xaa
```

TRANSPLANT MEDIA

This application is a continuation of U.S. application Ser. No. 09/917,340, filed Jul. 27, 2001, now issued as U.S. Pat. No. 6,696,238, which claims priority to U.S. provisional applications 60/221,632, filed Jul. 28, 2000, 60/249,602, filed Nov. 17, 2000, and 60/290,932, filed May 15, 2001.

FIELD OF THE INVENTION

The present invention relates to media comprising purified antimicrobial peptides, pore forming agents, and/or cell surface receptor binding compounds and their use for the storage and preservation of organs prior to transplant.

BACKGROUND OF THE INVENTION

A wide variety of organs, including kidneys, lungs, livers, hearts, pancreases, and small intestines are routinely and successfully transplanted. These organs are obtained either from living donors or from cadaveric sources.

In 1998, a total of 12,166 kidney transplants were performed in the United States by programs tracked by the UNOS Transplant Patient DataSource. A total of 45,189 people were on the waiting lists for kidneys as of Sep. 30, 1999. Over 20,000 kidneys were transplanted between Jul. 1, 1995 and Jun. 30, 1997. The graft survival rate for these transplanted kidneys was 93.4% after three months.

The ability to store organs for two or three days prior to transplantation allows sufficient time for histo-compatibility testing of donor and recipient, transport of the organ between transplant centers, preoperative preparation of the recipient, preliminary donor culture testing, and vascular repair of the organ if needed. The efficacy of organ transplantation depends in part on how well the organ is preserved prior to transplantation. Two methods are used to preserve organs prior to transplant: hypothermic storage and continuous pulsatile perfusion. Hypothermic storage by simple cold storage methods involves removal of an organ from a donor followed by rapid cooling. Cooling is achieved by a combination of external cooling and a short period of perfusion with a chilled medium to reduce the core temperature of the organ as quickly as possible. The organs are then immersed in a flush-out medium at from 0° C. to 4° C. Continuous pulsatile perfusion involves the continuous infusion of organs with a preservation solution designed to prevent low temperature injury.

A number of media have been developed for infusing and preserving organs prior to transplantation. Examples of such media include VIASPAN (also known as University of Wisconsin solution; Barr Laboratories, Pomona, N.Y.), University of Wisconsin Machine Perfusion Solution, Hypertonic Citrate Solution, histindine-tryptophan-glutarate solution (HTK Solution), HTK Solution of Bretschneider, Phosphate Buffered Sucrose, EuroCollins Solution, and Collins C2 Solution. However, none of these media are able to extend the preservation of organs past about 72 hours using cold storage methods. Additional preservation time would be useful for tests and for transportation of the organs. Furthermore, media that increase preservation time also can be expected to provide healthier organs for transplants performed within 72 hours.

Accordingly, what is needed in the art are improved media for preserving and storing organs prior to transplant. Such media should be able to extend the preservation period past 72 hours and provide organs with increased functionality upon transplant.

SUMMARY OF THE INVENTION

The present invention relates to media comprising antimicrobial polypeptides or pore forming agents and/or cell surface receptor binding compounds and their use for the storage and preservation of organs prior to transplant.

The present invention is not limited to any particular media or formulation. Indeed, a variety of medias and formulations are contemplated. In some embodiments, the present invention provides compositions comprising a purified antimicrobial polypeptide and hydroxyethyl starch. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In particularly preferred embodiments, the antimicrobial peptide is bovine dodecapeptide or BNP-1 (SEQ ID NO: 37). In some preferred embodiments, the antimicrobial polypeptide or defensin comprises D-amino acids. In some embodiments, the antimicrobial peptide and hydroxyethyl starch are in solution. The media of the present invention are not limited to any particular concentration of antimicrobial peptide. Indeed, a range of concentrations are contemplated (e.g., from about 0.01 to 1000 mg/l and preferably from about 0.1 to 5 mg/l). The present invention is not limited to any particular concentration of hydroxyethyl starch. Indeed, a range of concentrations are contemplated (e.g., from about 1 to 200 g/l). In some embodiments, the media further comprises a cell surface receptor binding compound. The present invention is not limited to any particular cell surface receptor binding compound. Indeed, a variety of cell surface receptor binding compounds are contemplated, including, but not limited to insulin-like growth factor 1 (IGF-1), epidermal growth factor (EGF), nerve growth factor (NGF), and substance P.

In other embodiments, the present invention provides compositions comprising an antimicrobial polypeptide and an impermeant anion selected from the group consisting of lactobionic acid and gluconate. In some preferred embodiments, the antimicrobial polypeptide and the impermeant ion are in solution. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In some preferred embodiments, the antimicrobial polypeptide or defensin comprises D-amino acids. In particularly preferred embodiments, the antimicrobial peptide is bovine dodecapeptide or BNP-1 (SEQ ID NO: 37). The media of the present invention are not limited to any particular concentration of antimicrobial peptide. Indeed, a range of concentrations are contemplated (e.g., from about 0.01 to 1000 mg/l and preferably from about 0.1 to 5 mg/l). The media of the present invention are not limited to any particular concentration of impermeant ion. Indeed, a range of concentrations are contemplated (e.g., from about 1 to 500 mM). In some embodiments, the media further comprises a cell surface receptor binding compound. The present invention is not limited to any particular cell surface receptor binding compound. Indeed, a variety of cell surface receptor binding compounds are contemplated, including, but not limited to IGF-1, EGF, NGF, and substance P. In some preferred embodiments, the media does not require the use of hydroxyethyl starch.

In other embodiments, the present invention provides compositions comprising an antimicrobial polypeptide and glutathione. In some preferred embodiments, the antimicrobial polypeptide and the impermeant ion are in solution. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In some preferred embodiments, the antimicrobial polypeptide or defensin comprises D-amino acids. In particularly preferred embodiments, the antimicrobial peptide is bovine dodecapeptide or BNP-1 (SEQ ID NO: 37). The media of the present invention are not limited to any particular concentration of antimicrobial peptide. Indeed, a range of concentrations are contemplated (e.g., from about 0.01 to 1000 mg/l and preferably from about 0.1 to 5 mg/l). The media of the present invention are not limited to any particular concentration of glutathione. Indeed, a range of concentrations are contemplated (e.g., from about 0.1 to 100 mM). In some embodiments, the media further comprises a cell surface receptor binding compound. The present invention is not limited to any particular cell surface receptor binding compound. Indeed, a variety of cell surface receptor binding compounds are contemplated, including, but not limited to IGF-1, EGF, NGF, and substance P. In some preferred embodiments, the media does not require the use of hydroxyethyl starch.

In further embodiments, the present invention provides compositions comprising a purified antimicrobial polypeptide and an ex vivo internal organ. The present invention is not limited to any particular internal organ. Indeed, a variety of internal organs are contemplated, including, but not limited to kidneys, hearts, lungs, small intestines, large intestines, livers, and pancreases. The present invention is not limited to organs from any particular species of animal. Indeed, use of organs from a variety of animals is contemplated, including organs from humans, pigs, and dogs. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In particularly preferred embodiments, the antimicrobial peptide is bovine dodecapeptide or BNP-1 (SEQ ID NO: 37). In some preferred embodiments, the antimicrobial polypeptide or defensin comprises D-amino acids. The media of the present invention are not limited to any particular concentration of antimicrobial peptide. Indeed, a range of concentrations are contemplated (e.g., from about 0.01 to 1000 mg/l and preferably from about 0.1 to 5 mg/l). In some embodiments, the compositions further comprise a macromolecular oncotic agent. The present invention is not limited to any particular macromolecular oncotic agent. Indeed, a variety of macromolecular oncotic agents are contemplated, including, but not limited to hydroxyethyl starch, dextran, and glucose. In other embodiments, the composition further comprises an impermeant anion. The present invention is not limited to any particular impermeant anion. Indeed, a variety of impermeant anions are contemplated, including, but not limited to, gluconate and lactobionic acid. In still further embodiments, the compositions comprise glutathione. In some embodiments, the compositions further comprise a cell surface receptor binding compound. The present invention is not limited to any particular cell surface receptor binding compound. Indeed, a variety of cell surface receptor binding compounds are contemplated, including, but not limited to IGF-1, EGF, NGF, and substance P. In some preferred embodiments, the media does not require the use of hydroxyethyl starch.

In still other embodiments, the present invention provides methods comprising a) providing cellular material and a solution comprising a purified antimicrobial polypeptide and b) storing the cellular material in said solution comprising a purified antimicrobial peptide. The present invention is not limited to the storage of any particular cellular material. Indeed, a variety of cellular materials are contemplated, including but not limited to internal organs, skin, and gametes. In some preferred embodiments, the cellular material is an internal organ. The present invention is not limited to any particular internal organ. Indeed, a variety of internal organs are contemplated, including, but not limited to kidneys, hearts, lungs, small intestines, large intestines, livers, and pancreases. The present invention is not limited to organs from any particular species of animal. Indeed, use of organs from a variety of animals is contemplated, including organs from humans, pigs, and dogs. In some embodiments, the internal organ is infused with the solution. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In particularly preferred embodiments, the antimicrobial peptide is bovine dodecapeptide or BNP-1 (SEQ ID NO: 37). In some preferred embodiments, the antimicrobial polypeptide or defensin comprises D-amino acids. The media of the present invention are not limited to any particular concentration of antimicrobial peptide. Indeed, a range of concentrations are contemplated (e.g., from about 0.01 to 1000 mg/l and preferably from about 0.1 to 5 mg/l). In some embodiments, the compositions further comprise a macromolecular oncotic agent. The present invention is not limited to any particular macromolecular oncotic agent. Indeed, a variety of macromolecular oncotic agents are contemplated, including, but not limited to hydroxyethyl starch, dextran, and glucose. In other embodiments, the composition further comprises an impermeant anion. The present invention is not limited to any particular impermeant anion. Indeed, a variety of impermeant anions are contemplated, including, but not limited to, gluconate and lactobionic acid. In still further embodiments, the compositions comprise glutathione. In some embodiments, the compositions further comprise a cell surface receptor binding compound. The present invention is not limited to any particular cell surface receptor binding compound. Indeed, a variety of cell surface receptor binding compounds are contemplated, including, but not limited to IGF-1, EGF, NGF, and substance P. In some preferred embodiments, the media does not require the use of hydroxyethyl starch.

In still further embodiments, the present invention provides compositions comprising a cell surface receptor binding compound and hydroxyethyl starch. The present invention is not limited to any particular cell surface receptor binding compound. Indeed, a variety of cell surface receptor binding compounds are contemplated, including, but not limited to IGF-1, EGF, NGF, and substance P.

In other embodiments, the present invention provides compositions comprising a cell surface receptor binding compound and an internal organ. In some embodiments, the compositions further comprise a macromolecular oncotic agent. The present invention is not limited to any particular macromolecular oncotic agent. Indeed, a variety of macromolecular oncotic agents are contemplated, including, but not limited to hydroxyethyl starch, dextran, and glucose. In other embodiments, the composition further comprises an impermeant anion. The present invention is not limited to any particular impermeant anion. Indeed, a variety of impermeant anions are contemplated, including, but not limited to, gluconate and lactobionic acid. In still further embodiments, the compositions comprise glutathione. In some preferred embodiments, the media does not require the use of hydroxyethyl starch.

In some embodiments, the present invention provides compositions comprising trehalose and hydroxyethyl starch. In some preferred embodiments, the trehalose and hydroxyethyl starch are in solution. The present invention is not limited to any particular concentration of trehalose. Indeed, a range of concentrations are contemplated (e.g., from about 1 mM to 30 mM). In some embodiments, the compositions further comprise an antimicrobial peptide and/or cell surface receptor binding compound. In some embodiments, the compositions further comprise a cell surface receptor binding compound. The present invention is not limited to any particular cell surface receptor binding compound. Indeed, a variety of cell surface receptor binding compounds are contemplated, including, but not limited to IGF-1, EGF, NGF, and substance P. The present invention is not limited to any particular antimicrobial peptide. Indeed a variety of antimicrobial peptides are contemplated, including, but not limited to, those identified by SEQ ID NOs:1-96. In some preferred embodiments, the antimicrobial peptide is a defensin. The present invention is not limited to any particular defensin. Indeed, the use of a variety of defensins is contemplated, including, but not limited to those identified by SEQ ID NOs:37-96. In particularly preferred embodiments, the antimicrobial peptide is bovine dodecapeptide or BNP-1 (SEQ ID NO: 37). The media of the present invention are not limited to any particular concentration of antimicrobial peptide. Indeed, a range of concentrations are contemplated (e.g., from about 0.01 to 1000 mg/l and preferably from about 0.1 to 5 mg/l). In some embodiments, the compositions further comprise a macromolecular oncotic agent. The present invention is not limited to any particular macromolecular oncotic agent. Indeed, a variety of macromolecular oncotic agents are contemplated, including, but not limited to hydroxyethyl starch, dextran, and glucose. In other embodiments, the composition further comprises an impermeant anion. The present invention is not limited to any particular impermeant anion. Indeed, a variety of impermeant anions are contemplated, including, but not limited to, gluconate and lactobionic acid. In still further embodiments, the compositions comprise glutathione.

In other embodiments, the present invention provides a kit comprising a vessel containing a solution comprising a compound selected from the group consisting of lactobionate and hydroxyethyl starch; and a vessel containing an antimicrobial polypeptide. In some embodiments, the antimicrobial polypeptide is BNP-1. In other embodiments, the vessel containing an antimicrobial polypeptide further comprises a cell surface receptor binding compound. In further embodiments, the cell surface receptor binding compound is selected from the group consisting of IGF-1, EGF, NGF, and substance P. In some embodiments, the kit further comprises instructions for combining said solution and the antimicrobial polypeptide.

In still further embodiments, the present invention provides processes for producing a storage solution comprising providing a solution comprising a compound selected from the group consisting of hydroxyethyl starch and lactobionate and a purified antimicrobial polypeptide; and combining said solution with the purified antimicrobial polypeptide. In some embodiments, the method further comprising the steps of providing at least one cell surface receptor binding compound and combining the at least one cell surface receptor binding compound with the solution and the antimicrobial polypeptide.

In some preferred embodiments, the present invention provides a composition comprising hydroxyethyl starch or lactobionate and an antimicrobial polypeptide for use as an organ storage or perfusion solution. In some embodiments, the composition further comprising a cell surface receptor binding compound. In other preferred embodiments, the present invention provides a composition comprising a purified antimicrobial polypeptide (e.g., BNP-1) and at least one purified cell surface receptor binding compound (e.g., IGF-1, EGF, NGF, and substance P), for use as a supplement for organ storage solutions.

In some embodiments, the media described herein further comprise a microtubule stabilizing agent selected from the group consisting of taxol, discodermolide, epothilone A and B, vinblastine, and vinchristine.

In still further embodiments, the present invention provides methods and compositions for stabilizing microtubules in cells, tissues, or organs, either in vitro, in vivo, or ex vivo. In preferred embodiments, the compositions comprise a defensin (e.g., BNP-1). In other preferred embodiments, the compositions comprise a cell surface receptor binding compound, impermeant anion, energy source, or macromolecular oncotic agent as described in more detail above. In other particularly preferred embodiments, the present invention provides a composition comprising a defensin (e.g., BNP-1) for use in stabilizing microtubules and/or actin filaments. In still other embodiments, the present invention provides methods and processes comprising providing a cell, tissue or organ, and a composition comprising a purified defensin, and treating the cell, tissue, or organ under conditions such that the cytoskeleton of the cell tissue, or organ is stabilized. In particularly preferred embodiments, microtubules and and/or actin filaments are stabilized. In still other particularly preferred embodiments, the defensin id BNP-1 (SEQ ID NO: 37).

In still further embodiments, the present invention provides a composition substantially as described in any of the examples herein.

DEFINITIONS

Figure 1:
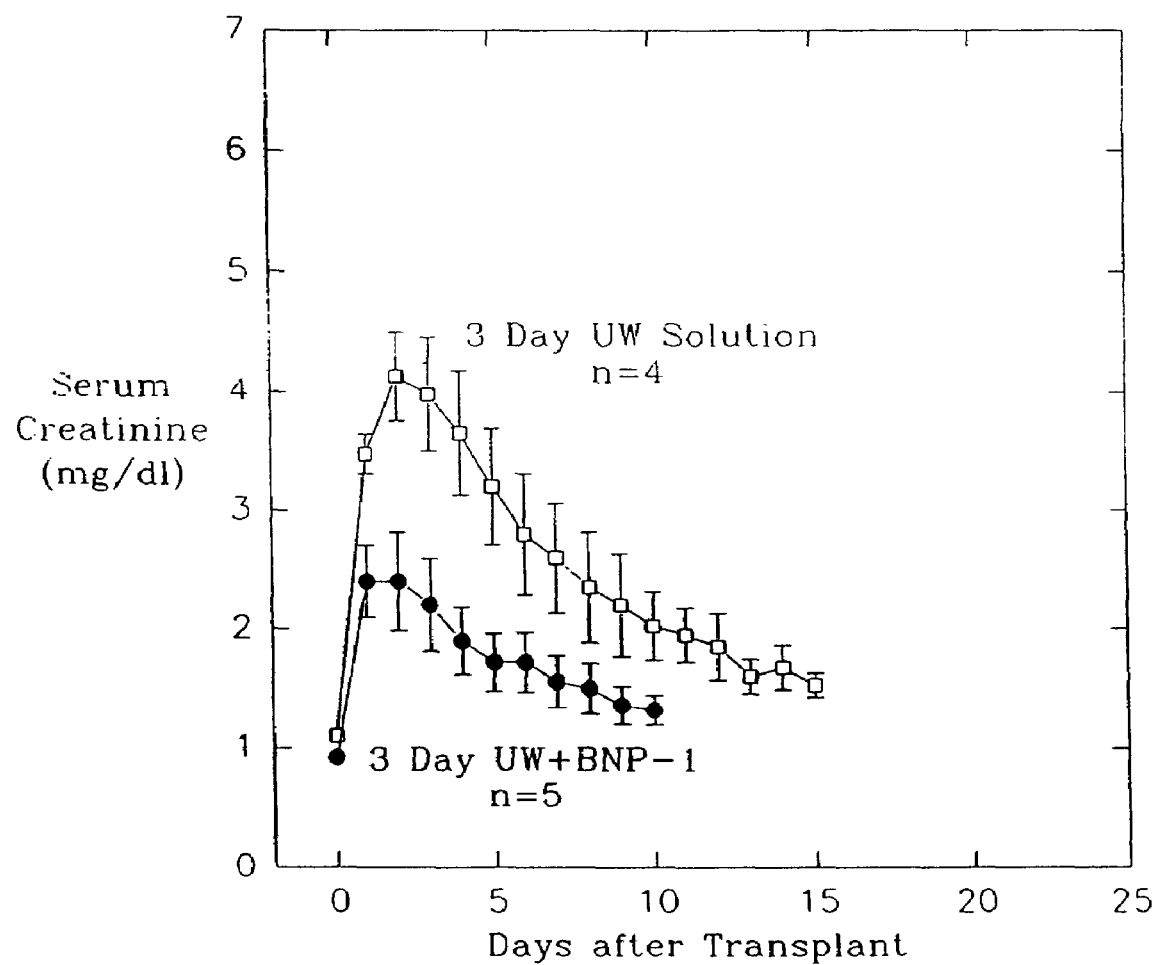
FIG. 1 is a graph showing serum creatinine levels (Y-axis) over time (X-axis) in dogs receiving kidneys stored for 3 days in UW solution alone (solid line) or in UW solution supplemented with BNP-1 (dashed line).

To facilitate understanding of the invention, a number of terms are defined below.

As used herein, the term "antimicrobial polypeptide" refers to polypeptides that inhibit the growth of microbes (e.g., bacteria). Examples of antimicrobial polypeptides include, but are not limited to, the polypeptides described in Table 1 below (e.g., defensins). Antimicrobial polypeptides include peptides synthesized from both L-amino and D-amino acids.

As used herein, the term "pore forming agent" refers to any agent (e.g., peptide or other organic compound) that forms pores in a biological membrane. When the pore forming agent is a peptide, the peptide can be synthesized from both L-amino and D-amino acids.

As used herein, the term "cell surface receptor binding compound" refers to any compound that directly or indirectly (e.g., binding through an intermediate agent) binds to a cell surface receptor (e.g., an agonist). Cell surface receptor binding compounds can be proteins (e.g., IGF-1 [insulin-like growth factor 1], IGF-2 [insulin-like growth factor 2], NGF-β[nerve growth factor-β], EGF [epidermal growth factor], CSGF [colony-stimulating growth factor], FGF [fibroblast growth factor], PDGF [platelet-derived growth factor], VEGF [vascular endothelial growth factor], TGF-β [transforming growth factor β], and bone morphogenetic proteins), either purified from natural sources or genetically engineered, as well as fragments, mimetics, derivatives or modifications thereof, and other organic compounds that bind to cell surface receptors (e.g., prostaglandins). Further examples of cell surface receptor binding compounds are provided in U.S. Pat. Nos. 5,183,805; 5,218,093; 5,130,298; 5,639,664; 5,457,034; 5,210,185; 5,470828; 5,650,496; 5,998,376; and 5,410,019; all of which are incorporated herein by reference.

As used herein, the term "cellular material" refers to any material or composition comprising cells (e.g., cultured cells, gametes (i.e., sperm and eggs), embryos, tissues, organs, and organisms).

As used herein, the term "internal organ" refers to an organ located in the interior of the body (e.g., in the thoracic or abdominal cavity). Examples of internal organs include, but are not limited to kidneys, hearts, lungs, small intestines, large intestines, livers, and pancreases. Internal organs can be provided from a human donor (either cadaveric or living) or be from an animal (e.g., for xenotransplants or transplant studies in an animal model such as dogs).

As used herein, the term "delayed graft function" refers to the delay in the return to normal serum creatinine following kidney transplant.

As used herein, the term "impermeant anion" refers to compounds that counteract swelling in organs that have been exposed to hypothermic temperatures. Examples of impermeant anions include, but are not limited to, gluconate and lactobionic acid.

As used herein, the term "macromolecular oncotic agent" refers to compounds used to maintain oncotic pressure equivalent to that of blood plasma. Examples of macromolecular oncotic agents include, but are not limited to, hydroxyethyl starch, dextran, trehalose, raffinose, mannitol, sucrose and glucose.

The term "recombinant protein" or "recombinant polypeptide" as used herein refers to a protein molecule expressed from a recombinant DNA molecule. In contrast, the term "native protein" or "native polypeptide" is used herein to indicate a protein isolated from a naturally occurring (i.e., a nonrecombinant) source. Molecular biological techniques may be used to produce a recombinant form of a protein or polypeptide with similar or identical properties as compared to the native form of the protein.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein in reference to an amino acid sequence or a protein, the term "portion" (as in "a portion of an amino acid sequence") refers to fragments of that protein. The fragments may range in size from four amino acid residues to the entire amino acid sequence minus one amino acid (e.g., 5, 6, 7, 8, . . . x–1).

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased protein function or increased protein function.

As used herein, the term "fusion protein" refers to a chimeric protein containing the protein of interest (e.g., defensins and fragments thereof) joined to a heterologous protein fragment (e.g., the fusion partner which consists of a non-defensin protein). The fusion partner may enhance the solubility of a defensin as expressed in a host cell, may provide an affinity tag to allow purification of the recombinant fusion protein from the host cell or culture supernatant, or both. If desired, the fusion protein may be removed from the protein of interest (e.g., defensin or fragments thereof) by a variety of enzymatic or chemical means know to the art.

As used herein, the term "purified" refers to molecules, either nucleic or amino acid sequences, that are removed from their natural environment, isolated or separated. The percent of a purified component is thereby increased in the sample. For example, an "isolated defensin" is therefore a purified defensin. "Substantially purified" molecules are at least 60% free, preferably at least 75% free, and more preferably at least 90% free from other components with which they are naturally associated.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

The term "homology" refers to a degree of complementarity. There may be partial homology or complete homology (i.e., identity). A partially complementary sequence is one that at least partially inhibits a completely complementary sequence from hybridizing to a target nucleic acid. This situation is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity). In this case, in the absence of non-specific binding, the probe will not hybridize to the second non-complementary target.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989, *Nucleic Acid Hybridization, A Practical Approach*, IRL Press, Washington D.C., 1985, for a general discussion of the state of the art).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5× SSPE (43.8 µl NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

As used herein, the term "$T_m$" is used in reference to the "melting temperature". The melting temperature is the temperature at which 50% of a population of double-stranded nucleic acid molecules becomes dissociated into single strands. The equation for calculating the Tm of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C.+(number of G+C)×4° C.]. (C. R. Newton et al., PCR, 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m=81.5+0.41(\% G+C)$, when a nucleic acid is in aqueous solution at 1 M NaCl. (e.g., Anderson and Young, Quantitative Filter Hybridization, in *Nucleic Acid Hybridization* (1985). Other more sophisticated computations exist in the art which take structural as well as sequence characteristics into account for the calculation of $T_m$. A calculated $T_m$ is merely an estimate; the optimum temperature is commonly determined empirically.

As used herein, the term "vector" is used in reference to nucleic acid molecules that transfer DNA segment(s) from one cell to another and capable of replication in a cell. Vectors may include plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in host cells and possibly other sequences, e.g., an optional operator sequence. A promoter is defined as a DNA sequence that directs RNA polymerase to bind to DNA and to initiate RNA synthesis. Eukaryotic expression vectors include a promoter, polyadenlyation signal and optionally an enhancer sequence.

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

The terms "buffer" or "buffering agents" refer to materials which when added to a solution, cause the solution to resist changes in pH.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The term "solution" refers to an aqueous mixture.

The term "buffering solution" refers to a solution containing a buffering reagent.

DETAILED DESCRIPTION OF THE INVENTION

The present invention relates to media comprising antimicrobial polypeptides and/or cell surface receptor binding compounds and their use for the storage and preservation of organs prior to transplant, and indeed, the preservation and storage of cellular materials in general. The media provided herein are superior to previously described media for organ preservation. Animals receiving kidneys stored in the media of the present invention for either three or four days had serum creatinine levels of less than half of those observed in control animals receiving kidneys stored in UW solution alone. Therefore, it is contemplated that the use of the media of the present invention to preserve organs prior to transplant results both in improved function of the organ after transplant and an increase in the length of time for which the organs can be stored (i.e., increased storage capability).

Lowered serum creatinine levels are indicative of healthier kidneys and a more preferable prognosis for the transplant patient. It is contemplated that transplant of healthier organs leads to a decrease in chronic rejection. Chronic rejection is a host versus graft rejection that occurs over a period of months to years, and is characterized by arterial and arteriolar thickening, atrophy, and fibrosis. Chronic rejection is the most common type of rejection for most solid organ allografts. In fact, approximately ten percent of kidney transplants fail each year due to chronic rejection. A 1999 survey indicates that a majority of transplant physicians and surgeons believe that chronic rejection is the area of transplant medicine that needs the most improvement (www.kidney.org/general/news/survey.cfm).

Additionally, use of the media of the present invention for cold storage or machine perfusion is expected to greatly reduce costs associated with delayed graft function in kidneys. Most kidney transplant centers currently experience delayed graft function rates of between 20% and 30%. When kidneys from non-beating heart donors are utilized, the rate of delayed graft function increases to approximately 75%-90%. Delayed graft function has been estimated to add up to $20,000.00 to the cost of a kidney transplant due to dialysis, complications, and longer hospital stay. Furthermore, the incidence of delayed graft function is correlated with chronic rejection (i.e., 53% of kidneys in patients that need dialysis survive 5 years vs. 80% in optimal kidneys). The experimental data provided below in the Examples demonstrates that use of the media compositions of the present invention greatly reduces the time required to return to normal serum creatinine levels and thus reduces the incidence of delayed graft function.

Furthermore, it is expected that the media of the present invention will also be useful for the storage and/or resuscitation of kidneys from non-beating heart donors so that they can routinely be used for transplant. As described above, the delayed graft function rates associated with kidneys from non-beating heart donors exceeds 75%. The major source of delayed graft function of these kidneys is believed to be warm ischemic injury. Most cold storage methods have been completely unsuccessful in reducing preservation injury and delayed graft function. As a result, kidneys from non-beating heart donors that are subject to warm ischemic injury represent the largest untapped source of donor kidneys. It is contemplated that the use of the media of the present invention will facilitate routine use of kidneys from non-beating heart donors, thus greatly expanding the pool of kidneys available to recipients. In particular, the use of the media of the present invention to store kidneys from non-beating heart donors will result in a decrease in the delayed graft function rates normally observed when those kidneys are utilized for transplant.

Accordingly, improved compositions and methods for organ transplant are described in detail below.

I. Transplant Media

The present invention contemplates the addition of antimicrobial polypeptides (e.g., defensins) and/or cell surface receptor binding compounds to media used for organ transplantation and other procedures such as cardioplegia. In Section A, antimicrobial peptides useful in the media of the present invention are described. In Section B, cell surface receptor binding compounds useful in the present invention are described. In Section C, other components of organ transplantation media are described and representative formulas for organ preservation media are provided.

A. Antimicrobial Peptides

In some embodiments of the present invention, compositions for preserving organs prior to transplantation are provided. In some embodiments of the present invention, media for preserving organs comprise one or more antimicrobial polypeptides (e.g., *Antimicrobial Peptide Protocols*, ed. W.

M. Shafer, Humana Press, Totowa, N.J. [1997]) or pore forming agents. In some embodiments, the antimicrobial peptide or pore forming agent is a compound or peptide selected from the following: magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+[K10E, F12W-magainin-2], MG4+[F12W-magainin 2], MG6+[f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(+/−) 1-(4-aminobutyl)-6-benzylindane], PM2c [(+/−) -6-benzyl-1-(3-carboxypropyl)indane], PM3 [(+/−)1-benzyl-6-(4-aminobutyl)indane], tachyplesin, buforin I or II, misgurin, melittin, PR-39, PR-26, 9-phenylnonylamine, (KLAKiKLA)n (SEO ID NO: 97), (KLAK-LAK)n (SEO ID NO: 98), where n=1, 2, or 3, (KALKALK)3 (SEO ID NO: 99), KLGKKLG)n (SEO ID NO: 100), and KAAKKAA)n (SEO ID NO: 101), wherein N+1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG 1, 1bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from or comprise D-amino acids.

The compounds listed above can be isolated and purified from natural sources as appropriate. The compounds may also be produced recombinantly or synthetically as described below. In some embodiments, the antimicrobial peptide is included in the media at a concentration sufficient to lower serum creatinine levels in kidney transplant recipients as compared to recipients of kidneys stored without antimicrobial peptides. In other embodiments, the antimicrobial polypeptide is included in the media at a concentration sufficient to cause a decrease in delayed graft function rates of kidneys stored in the media as compared to unsupplemented media. Preferably, the time for return to baseline serum creatinine levels is improved by at least 25%, and most preferably by at least 50%, as compared to control unsupplemented media. In preferred embodiments, the media of the present invention comprise one or more antimicrobial polypeptides at a concentration of about 0.01 to 1000 mg/L. In particularly preferred embodiments, the media comprises a solution comprising one or more antimicrobial polypeptides at a concentration of about 0.1 to 5 mg/L.

The present invention is not limited to a particular mechanism of action. Indeed, an understanding of the mechanism of action is not necessary to practice the present invention. Nevertheless, the data summarized in Example 10 demonstrates that the addition of an antimicrobial polypeptide to standard organ storage solutions (e.g., UW solution) results in both the stabilization of cytoskeletal structure and an increased ability of the cytoskeleton to reassemble upon reperfusion. It is particularly notable that the antimicrobial polypeptide stabilized both actin filaments and microtubules.

In some embodiments of the present invention, the antimicrobial polypeptide is a defensin. In preferred embodiments, the compositions of the present invention comprise one or more defensins. In further preferred embodiments, the composition comprises a solution comprising purified defensins at a concentration of about 0.01 to 1000 mg/L. In particularly preferred embodiments, the media comprises a solution comprising defensins at a concentration of about 0.1 to 5 mg/L. In still further preferred embodiments, the antimicrobial polypeptide is BNP1 (also known as bactanecin and bovine dodecapeptide). In certain embodiments, the defensin comprises the following consensus sequence: (SEQ ID NO:96 —$X_1CN_1CRN_2CN_3ERN_4CN_5GN_6CCX_2$, wherein N and X represent conservatively or nonconservatively substituted amino acids and $N_1=1$, $N_2=3$ or 4, $N_3=3$ or 4, $N_4=1$, 2, or 3, $N_6=5-9$, $X_1$ and $X_2$ may be present, absent, or equal from 1-2.

The present invention is not limited to any particular defensin. Indeed, media comprising a variety of defensins are contemplated. Representative defensins are provided in Tables 1 and 2 below. In general, defensins are a family of highly cross-linked, structurally homologous antimicrobial peptides found in the azurophil granules of polymorphonuclear leukocytes (PMN's) with homologous peptides being present in macrophages (e.g., Selsted et al., Infect. Immun. 45:150-154 [1984]). Originally described as "Lysosomal Cationic Peptides" in rabbit and guinea pig PMN (Zeya et al., Science 154:1049-1051 [1966]; Zeya et al., J. Exp. Med. 127:927-941 [1968]; Zeya et al., Lab. Invest. 24:229-236 [1971]; Selsted et al., [1984], supra.), this mixture was found to account for most of the microbicidal activity of the crude rabbit PMN extract against various microorganisms (Zeya et al., [1966], supra; Lehrer et al., J. Infect. Dis. 136:96-99 [1977]; Lehrer et al., Infect. Immun. 11:1226-1234 [1975]). Six rabbit neutrophil defensins have been individually purified and are designated NP-1, NP-2, NP-3A, NP-3B, NP-4, and NP-5. Their amino acid sequences were determined, and their broad spectra of activity were demonstrated against a number of bacteria (Selsted et al., Infect. Immun. 45:150-154 [1984]), viruses (Lehrer et al., J. Virol. 54:467 [1985]), and fungi (Selsted et al., Infect. Immun. 49:202-206 [1985]; Segal et al., 151:890-894 [1985]). Defensins have also been shown to possess mitogenic activity (e.g., Murphy et al., J. Cell. Physiol. 155:408-13 [1993]).

Four peptides of the defensin family have been isolated from human PMN's and are designated HNP-1, HNP-2, HNP-3, and HNP-4 (Ganz et al., J. Clin. Invest. 76:1427-1435 [1985]; Wilde et al., J. Biol. Chem. 264:11200-11203 [1989]). The amino acid sequences of HNP-1, HNP-2, and HNP-3 differ from each other only in their amino terminal residues, while each of the human defensins are identical to the six rabbit peptides in 10 or 11 of their 29 to 30 residues. These are the same 10 or 11 residues that are shared by all six rabbit peptides. Human defensin peptides have been shown to share with the rabbit defensins a broad spectrum of antimicrobial activity against bacteria, fungi, and enveloped viruses (Ganz et al., [1985], supra).

Three defensins designated RatNP-1, RatNP-2, and RatNP-4, have been isolated from rat (Eisenhauer et al., Infection and Immunity 57:2021-2027 [1989]). A guinea pig defensin (GPNP) has also been isolated, purified, sequenced and its broad spectrum antimicrobial properties verified (Selsted et al., Infect. Immun. 55:2281-2286 [1987]). Eight of its 31 residues were among those invariant in six rabbit and three human defensin peptides. The sequence of GPNP also included three nonconservative substitutions in positions otherwise invariant in the human and rabbit peptides. Of the defensins tested in a quantitative assay HNP-1, RatNP-1, and rabbit NP-1 possess the most potent antimicrobial properties, while NP-5 possesses the least amount of antimicrobial activity when tested against a panel of organisms in stationary growth phase (Selsted et al., Infect. Immun. 45:150-154 [1984]; Ganz et al., J. Clin. Invest. 76:1427-1435 [1985]). Defensin peptides are further described in U.S. Pat. Nos. 4,543,252; 4,659,692; and 4,705,777 (each of which is incorporated herein by reference).

Accordingly, in some embodiments, the media comprises one or more defensins selected from the group consisting of SEQ ID NOs: 37-95. In particularly preferred embodiments, the media comprises bovine defensin peptide (BNP-1; SEQ ID NO: 37, Romeo et al., J. Biol. Chem. 263(15):9573-9575 [1988]). In some embodiments, the defensin is included in the media at a concentration sufficient to lower serum creatinine levels in kidney transplant recipients as compared to recipients of kidneys stored without defensin peptides.

Defensin peptides suitable for use in the methods and compositions of the present invention include natural defensin peptides isolated from known cellular sources, synthetic peptides produced by solid phase or recombinant DNA techniques, and defensin analogs which may be smaller peptides or other molecules having similar binding and biological activity as the natural defensin peptides (e.g., peptide mimetics). Methods for the purification of defensin peptides are described in U.S. Pat. Nos. 4,543,252; 4,659,692; and 4,705,777, the disclosures of which are incorporated herein by reference.

In preferred embodiments, suitable synthetic peptides will usually comprise all or part of the amino acid sequence of a known peptide, more preferably incorporating at least some of the conserved regions identified in Table 2. In particularly preferred embodiments, the synthetic peptides incorporate at least one of the conserved regions, more usually incorporating two of the conserved regions, preferably conserving at least three of the conserved regions, and more preferably conserving four or more of the conserved regions. In preferred embodiments, the synthetic peptides comprise fifty amino acids or fewer, although there may be advantages in increasing the size of the peptide above that of the natural peptides in certain instances. In certain embodiments, the peptides have a length in the range from about 10 to 50 amino acids, preferably being in the range from about 10 to 40 amino acids, and most preferably being in the range from about 30 to 35 amino acids which corresponds generally to the length of the natural defensin peptides.

In some cases, it may be desirable to incorporate one or more non-natural amino acids in the synthetic defensin peptides of the present invention. In preferred embodiments, non-natural amino acids comprise at least an N-terminus and a C-terminus and have side chains that are either identical to or chemically modified or substituted from a natural amino acid counterpart. An example of a non-natural amino acid is an optical isomer of a naturally-occurring L-amino acid, such as a peptide containing all D-amino acids. Examples of the synthesis of peptides containing all D-amino acids include Merrifield et al., Ciba Found Symp. 186:5-26 (1994); Wade et al., Proc. Natl. Acad. Sci. USA 87(12):4761-5 (1990); and U.S. Pat. No. 5,792,831, which is herein incorporated by reference. Examples of chemical modifications or substitutions include hydroxylation or fluorination of C—H bonds within natural amino acids. Such techniques are used in the manufacture of drug analogs of biological compounds and are known to one of ordinary skill in the art.

Synthetic peptides having biological and binding activity the same or similar to that of natural defensin peptides may be produced by either of two exemplary approaches. First, the polypeptides may be produced by the well-known Merrifield solid-phase chemical synthesis method wherein amino acids are sequentially added to a growing chain (Merrifield (1963) J. Am. Chem. Soc. 85:2149-2156 [1963]). Automatic peptide synthesis equipment is available from several commercial suppliers, including PE Biosystems, Inc., Foster City, Calif.; Beckman Instruments, Inc., Waldwick, N.J.; and Biosearch, Inc., San Raphael, Calif. Using such automatic synthesizers according to manufacturer's instructions, peptides may be produced in gram quantities for use in the present invention.

Second, the synthetic defensin peptides of the present invention may be synthesized by recombinant techniques involving the expression in cultured cells of recombinant DNA molecules encoding a gene for a desired portion of a natural or analog defensin molecule. The gene encoding the defensin peptide may itself be natural or synthetic. Conveniently, polynucleotides may be synthesized by well known techniques based on the desired amino acid sequence. For example, short single-stranded DNA fragments may be prepared by the phosphoramidite method (Beaucage et al., Tetra. Lett. 22:1859-1862 [1981]). A double-stranded fragment may then be obtained either by synthesizing the complementary strand and annealing the strands together under appropriate conditions or by adding the complementary strand using DNA polymerase under appropriate conditions or by adding the complementary strand using DNA polymerase with an appropriate primer sequence. The natural or synthetic DNA fragments coding for the desired defensin peptide may then be incorporated in a suitable DNA construct capable of introduction to and expression in an in vitro cell culture. The DNA fragments can be portions or variants of wild-type nucleic acids encoding defensins. Suitable variants include those both with conservative and nonconservative amino acid substitutions.

The methods and compositions of the present invention may also employ synthetic non-peptide compositions that have biological activity functionally comparable to that of the known defensin peptides. By functionally comparable, it is meant that the shape, size, flexibility, and electronic configuration of the non-peptide molecule is such that the biological activity of the molecule is similar to the defensin peptides. In particular, the non-peptide molecules should display comparable mitogenic activity and/or antimicrobial activity or pore forming ability, preferably possessing both activities. Such non-peptide molecules will typically be small molecules having a molecular weight in the range from about 100 to 1000 daltons. The use of such small molecules is frequently advantageous in the preparation of pharmacological compositions. Candidate mimetics can be screened in large numbers to identify those having the desired activity.

The identification of such nonpeptide analog molecules can be performed using techniques known in the art of drug design. Such techniques include, but are not limited to, self-consistent field (SCF) analysis, configuration interaction (CI) analysis, and normal mode dynamics computer analysis, all of which are well described in the scientific literature (Rein et al., Computer-Assisted Modeling of Receptor-Ligand Interactions, Alan Liss, N.Y., [1989]). Preparation of the identified compounds will depend on the desired characteristics of the compounds and will involve standard chemical synthetic techniques (Cary et al., Advanced Organic Chemistry, part B, Plenum Press, New York [1983]).

TABLE 1

Antimicrobial Peptides

| SEQ ID NO: | Name | Organism | Sequence |
|---|---|---|---|
| 1 | lingual antimicrobial peptide precursor (Magainin) | Bos taurus | mrlhhlllallflvlsagsgftqgvrnsqscrrnkgicvp ircpgsmrqigtclgaqvkccrrk |
| 2 | antimicrobial peptide PGQ | Xenopus laevis | gvlsnvigylkklgtgalnavlkq |
| 3 | Xenopsin | Xenopus laevis | mykgiflcvllavicanslatpssdadedndeveryvrgw askigqtlgkiakvglkeliqpkreamlrsaeaqgkrpwil |
| 4 | magainin precursor | Xenopus laevis | mfkglficsliavicanalpqpeasadedmderevrgigk flhsagkfgkafvgeimkskrdaeavgpeafadedldere vrgigkflhsakkfgkafvgeimnskrdaeavgpeafade dlderevrgigkflhsakkfgkafvgeimnskrdaeavgp eafadedlderevrgigkflhsakkfgkafvgeimnskrd aeavgpeafadedfderevrgigkflhsakkfgkafvgei mnskrdaeavgpeafadedlderevrgigkflhsakkfgk afvgeimnskrdaeavddrrwve |
| 5 | tachyplesin I | Tachypleus gigas | kwcfrvcyrgicyrrcr |
| 6 | tachyplesin II | Tachypleus gigas | rwcfrvcyrgicyrkcr |
| 7 | buforin I | Bufo bufo gagarizans | msgrgkqggkvrakaktrssraglqfpvgrvhrllrkgny aqrvgagapvylaavleyltaeilelagnaardnkktrii prhlqlavrndeelnkllggvtiaqggvlpniqavllpkt esskpaksk |
| 8 | buforin II | Bufo bufo gagarizans | trssraglqfpvgrvhrllrk |
| 9 | cecropin A | Bombyx mori | mnfvrilsfvfalvlalgavsaapeprwklfkkiekvgrn vrdglikagpaiavigqakslgk |
| 10 | cecropin B | Bombyx mori | mnfakilsfvfalvlalsmtsaapeprwkifkkiekmgrn irdgivkagpaievlgsakaigk |
| 11 | cecropin C | Drosophila melanogaster | mnfykifvfvalilaisigqseagwlkklgkrierigqht rdatiqglgiaqqaanvaatarg |
| 12 | cecropin P1 | Sus scrofa | swlsktakklensakkrisegiaiaiqggpr |
| 13 | indolicidin | Bos taurus | ilpwkwpwwpwrr |
| 14 | nisin | Lactococcus lactis | itsislctpgcktgalmgcnmktatchcsihvsk |
| 15 | ranalexin | Rana catesbeiana | flgglikivpamicavtkkc |
| 16 | lactoferricin B | Bos taurus | fkcrrwqwrmkklgapsitcvrraf |
| 17 | protegrin-1 | Sus scrofa | rggrlcycrrrfcvcvgrx |
| 18 | protegrin-2 | Sus scrofa | ggrlcycrrrfcicvg |
| 19 | histatin precursor | Homo sapiens | mkffvfalilalmlsmtgadshakrhhgykrkfhekhhsh rgyrsnylydn |
| 20 | histatin 1 | Macaca fascicularis | dsheerhhgrhghhkygrkfhekhhshrgyrsnylydn |
| 21 | dermaseptin | Phyllomedusa sauvagei | alwktmlkklgtmalhagkaalgaaadtisqtq |
| 22 | dermaseptin 2 | Phyllomedusa sauvagei | alwftmlkklgtmalhagkaalgaaantisqgtq |
| 23 | dermaseptin 3 | Phyllomedusa sauvagei | alwknmlkgigklagkaalgavkklvgaes |
| 24 | misgurin | Misgurnus anguillicaudatus | rqrveelskfskkgaaarrrk |
| 25 | melittin | Apis mellifera | gigavlkvlttglpaliswisrkkrqq |
| 26 | pardaxin-1 | Pardachirus pavoninus | gffalipkiissplfktllsavgsalsssgeqe |
| 27 | pardaxin-2 | Pardachirus pavoninus | gffalipkiisspifktllsavgsalsssggqe |
| 28 | bactenecin 5 precursor | Bos taurus | metqraslslgrcslwllllglvlpsasaqalsyreavlr avdqfnersseanlyrlleldptpnddldpgtrkpvsfrv ketdcprtsqqpleqcdfkenglvkqcvgtvtldpsndqf dincnelqsvrfrppirrppirppfyppfrppirppifpp irppfrpplgpfpgrr |
| 29 | bactenecin precursor | Bos taurus | metpraslslgrwslwllllglalpsasaqalsyreavlr avdqlneqssepniyrlleldqppqddedpdspkrvsfrv ketvcsrttqqppeqcdfkengllkrcegtvtldqvrgnf ditcnnhqsiritkqpwappqaarlcrivvirvcr |
| 30 | ceratotoxin A | Ceratitis capitata | sigsalkkalpvakkigkialpiakaalp |
| 31 | ceratotoxin B | Ceratitis capitata | sigsafkkalpvakkigkaalpiakaalp |
| 32 | cathelicidin antimicrobial peptide | Homo sapiens | mktqrnghslgrwslvllllglvmplaiiaqvlsykeavl raidginqrssdanlyrlldldprptmdgdpdtpkpvsft |

TABLE 1-continued

Antimicrobial Peptides

| SEQ ID NO: | Name | Organism | Sequence |
|---|---|---|---|
| | | | vketvcprttqqspedcdfkkdglvkrcmgtvtlnqargs fdiscdkdnkrfallgdffrkskekigkefkrivqrikdf lrnlvprtes |
| 33 | myeloid cathelicidin 3 | Equus caballus | metqrntrclgrwsplllllglvippattqalsykeavlr avdglnqrssdenlyrlleldplpkgdkdsdtpkpvsfmv ketvcprimkqtpeqcdfkenglvkqcvgtvildpvkdyf dascdepqrvkrfhsvgsliqrhqqmirdkseatrhgiri itrpklllas |
| 34 | myeloid antimicrobial peptide BMAP-28 | Bos taurus | metqraslslgrwslwllllglalpsasaqalsyreavlr avdqlneksseanlyrlleldpppkeddenpnipkpvsfr vketvcprtsqqspeqcdfkengllkecvgtvtldqvgsn fditcavpqsvgglrslgrkilrawkkygpiivpiirig |
| 35 | myeloid cathelicidin 1 | Equus caballus | metqrntrclgrwsplllllglvippattqalsykeavlr avdglnqrssdenlyrlleldplpkgdkdsdtpkpvsfmv ketvcprimkqtpeqcdfkenglvkqcvgtvilgpvkdhf dvscgepqrvkrfgrlaksflrmrillprrkillas |
| 36 | SMAP 29 | Ovis aries | metqraslslgrcslwllllglalpsasaqvlsyreavlr aadqlneksseanlyrlleldpppkqddensnipkpvsfr vketvcprtsqqpaeqcdfkengllkecvgtvtldqvrnn fditcaepqsvrglrrlgrkiahgvkkygptvlriiriag |
| 37 | BNP-1 | Bos taurus | rlcrivvirvcr |
| 38 | HNP-1 | Homo sapiens | acycripaciagerrygtciyqgrlwafcc |
| 39 | HNP-2 | Homo sapiens | cycripaciagerrygtciyqgrlwafcc |
| 40 | HNP-3 | Homo sapiens | dcycripaciagerrygtciyqgrlwafcc |
| 41 | HNP-4 | Homo sapiens | vcscrlvfcrrtelrvgncliggvsftycctrv |
| 42 | NP-1 | Oryctolagus cuniculus | vvcacrralclprerragfcrirgrihplccrr |
| 43 | NP-2 | Oryctolagus cuniculus | vvcacrralclplerragfcrirgrihplccrr |
| 44 | NP-3A | Oryctolagus cuniculus | gicacrrrfcpnserfsgycrvngaryvrccsrr |
| 45 | NP-3B | Oryctolagus cuniculus | grcvcrkqllcsyrerrigdckirgvrfpfccpr |
| 46 | NP-4 | Oryctolagus cuniculus | vsctcrrfscgfgerasgsctvnggvrhtlccrr |
| 47 | NP-5 | Oryctolagus cuniculus | vfctcrgflcgsgerasgsctingvrhtlccrr |
| 48 | RatNP-1 | Rattus norvegicus | vtcycrrtrcgfrerlsgacgyrgriyrlccr |
| 49 | Rat-NP-3 | Rattus norvegicus | cscrysscrfgerllsgacrlngriyrlcc |
| 50 | Rat-NP-4 | Rattus norvegicus | actcrigacvsgerltgacglngriyrlccr |
| 51 | GPNP | Guinea pig | rrcicttrtcrfpyrrlgtcifqnrvytfcc |
| 52 | beta defensin-3 | Homo sapiens | mrihyllfallflflvpvpghggiintlqkyycrvrggrc avlsclpkeeqigkcstrgrkccrrkk |
| 53 | theta defensin-1 | Macaca mulatta | rcictrgfcrclcrrgvc |
| 54 | defensin CUA1 | Helianthus annuus | mkssmkmfaalllvvmcllanemggplvveartcesqshk fkgtclsdtncanvchserfsggkcrgfrrrcfctthc |
| 55 | defensin SD2 | Helianthus annuus | mkssmkmfaalllvvmcllanemggplvveartcesqshk fkgtclsdtncanvchserfsggkcrgfrrrcfctthc |
| 56 | neutrophil defensin 2 | Macaca mulatta | acycripaclagerrygtcfymgrvwafcc |
| 57 | 4 KDA defensin | Androctonus australis hector | gfgcpfnqgachrhcrsirrrggycaglfkqtctcyr |
| 58 | defensin | Mytilus galloprovincialis | gfgcpnnyqchrhcksipgrcggycggxhrlrctcyrc |
| 59 | defensin AMP1 | Heuchera sanguinea | dgvklcdvpsgtwsghcgssskcsqqckdrehfayggach yqfpsvkcfckrqc |
| 60 | defensin AMP1 | Clitoria ternatea | nlcerasltwtgncgntghcdtqcrnwesakhgachkrgn wkcfcyfnc |
| 61 | cysteine-rich cryptdin-1 homolog | Mus musculus | mkklvllfalvllafqvqadsiqntdeetkteeqpgekdq avsvsfgdpqgsalqdaalgwgrrcpqcprcpscpscprc prcprckcnpk |
| 62 | beta-defensin-9 | Bos taurus | qgvrnfvtcrinrgfcvpircpghrrqigtclgpqikccr |
| 63 | beta-defensin-7 | Bos taurus | qgvrnfvtcrinrgfcvpircpghrrqigtclgprikccr |
| 64 | beta-defensin-6 | Bos taurus | qgvrnhvtcriyggfcvpircpgrtrqigtcfgrpvkccrw |
| 65 | beta-defensin-5 | Bos taurus | qvvrnpqscrwnmgvcipiscpgnmrqigtcfgprvpccr |
| 66 | beta-defensin-4 | Bos taurus | qrvrnpqscrwnmgvcipflcrvgmrqigtcfgprvpccrr |
| 67 | beta-defensin-3 | Bos taurus | qgvrnhvtcrinrgfcvpircpgrtrqigtcfgprikccrsw |
| 68 | beta-defensin-10 | Bos taurus | qgvrsylscwgnrgiclnrcpgrmrqigtclaprvkccr |
| 69 | beta-defensin-13 | Bos taurus | sgisgplscgrnggvcipircpvpmrqigtcfgrpvkccrsw |

TABLE 1-continued

Antimicrobial Peptides

| SEQ ID NO: | Name | Organism | Sequence |
|---|---|---|---|
| 70 | beta-defensin-1 | Bos taurus | dfaschtnggiclpnrcpghmiqigicfrprvkccrsw |
| 71 | coleoptericin | Zophobas atratus | slqggapnfpqpsqqnggwqvspdlgrddkgntrgqieiq nkgkdhdfnagwgkvirgpnkakptwhvggtyrr |
| 72 | beta defensin-3 | Homo sapiens | mrihyllfallflflvpvpghggiintlqkyycrvrggrc avlsclpkeeqigkcstrgrkccrrkk |
| 73 | defensin C | Aedes aegypti | atcdllsgfgvgdsacaahciargnrggycnskkvcvcrn |
| 74 | defensin B | Mytilus edulis | gfgcpndypchrhcksipgryggycggxhrlrctc |
| 75 | sapecin C | Sarcophaga peregrina | atcdllsgigvqhsacalhcvfrgnrggyctgkgicvcrn |
| 76 | macrophage antibiotic peptide MCP-1 | Oryctolagus cuniculus | mrtlallaaillvalqaqaehvsvsidevvdqqppqaedq dvaiyvkehessalealgvkagvvcacrralclprerrag fcrirgrihplccrr |
| 77 | cryptdin-2 | Mus musculus | mkplvllsalvllsfqvqadpiqntdeetkteeqsgeedq avsvsfgdregaslqeeslrdlvcycrtrgckrrermngt crkghlmytlcc |
| 78 | cryptdin-5 | Mus musculus | mktfvllsalvllafqvqadpihktdeetnteeqpgeedq avsisfggqegsalheelskklicycrirgckrrervfgt crnlfltfvfccs |
| 79 | cryptdin 12 | Mus musculus | lrdlvcycrargckgrermngtcrkghllymlccr |
| 80 | defensin | Pyrrhocoris apterus | atcdilsfqsqwvtpnhagcalhcvikgykggqckitvchcrr |
| 81 | defensin R-5 | Rattus norvegicus | vtcycrstrcgfrerlsgacgyrgriyrlccr |
| 82 | defensin R-2 | Rattus norvegicus | vtcscrtsscrfgerlsgacrlngriyrlcc |
| 83 | defensin NP-6 | Oryctolagus cuniculus | gicacrrrfclnfeqfsgycrvngaryvrccsrr |
| 84 | beta-defensin-2 | Pan troglodytes | mrvlyllfsflfiflmplpgvfggisdpvtclksgaichp vfcprrykqigtcglpgtkcckkp |
| 85 | beta-defensin-2 | Homo sapiens | mrvlyllfsflfiflmplpgvfggigdpvtclksgaichp vfcprrykqigtcglpgtkcckkp |
| 86 | beta-defensin-1 | Homo sapiens | mrtsylllftlclllsemasggnfltglghrsdhyncvss ggqclysacpiftkiqgtcyrgkakcck |
| 87 | beta-defensin-1 | Capra hircus | mrlhhlllvlfflvlsagsgftqgirsrrschrnkgvcal trcprnmrqigtcfgppvkccrkk |
| 88 | beta defensin-2 | Capra hircus | mrlhhlllalfflvlsagsgftqgiinhrscyrnkgvcap arcprnmrqigtchgppvkccrkk |
| 89 | defensin-3 | Macaca mulatta | mrtlvilaaillvalqaqaeplqartdeataaqeqiptdn pevvvslawdeslapkdsvpglrknmacycripaclager rygtcfyrrrvwafcc |
| 90 | defensin-1 | Macaca mulatta | mrtlvilaaillvalqaqaeplqartdeataaqeqiptdn pevvvslawdeslapkdsvpglrknmacycripaclager rygtcfylgrvwafcc |
| 91 | neutrophil defensin 1 | Mesocricetus auratus | vtcfcrrrgcasrerhigycrfgntiyrlccrr |
| 92 | neutrophil defensin 1 | Mesocricetus auratus | cfckrpvcdsgetqigycrlgntfyrlccrq |
| 93 | Gallinacin 1-alpha | Gallus gallus | grksdcfrkngfcaflkcpyltlisgkcsrfhlcckriw |
| 94 | defensin | Allomyrina dichotoma | vtcdllsfeakgfaanhslcaahclaigrrggscergvcicrr |
| 95 | neutrophil cationic peptide 1 | Cavia porcellus | rrcicttrtcrfpyrrlgtcifqnrvytfcc |

TABLE 2

Defensins

| SEQ ID NO | Name | Organism | Sequence |
|---|---|---|---|
| 38 | HNP-1 | Human | ACYCRIPACIAGERRYGTCIYQGRLWAFCC |
| 39 | HNP-2 | Human | CYCRIPACIAGERRYGTCIYQGRLWAFCC |
| 40 | HNP-3 | Human | DCYCRIPACIAGERRYGTCIYQGRLWAFCC |
| 41 | HNP-4 | Human | VCSCRLVFCRRTELRVGNCLIGGVSFTYCCTRV |
| 42 | NP-1 | Rabbit | VVCACRRALCLPRERRAGFCRIRGRIHPLCCR |
| 43 | NP-2 | Rabbit | VVCACRRALCLPLERRAGFCRIRGRIHPLCCRR |
| 44 | NP-3A | Rabbit | GICACRRRFCPNSERFSGYCRVNGARYVRCCSRR |
| 45 | NP-3B | Rabbit | GRCVCRKQLLCSYRERRIGDCKIRGVRFPFCCPR |
| 46 | NP-4 | Rabbit | VSCTCRRFSCGFGERASGSCTVNGVRHTLCCRR |
| 47 | NP-5 | Rabbit | VFCTCRGFLCGSGERASGSCTINGVRHTLCCRR |
| 48 | RatNP-1 | Rat | VTCYCRRTRCGFRERLSGACGYRGRIYRLCCR |

TABLE 2-continued

Defensins

| SEQ ID NO | Name | Organism | Sequence |
|---|---|---|---|
| 49 | Rat-NP-3 | Rat | CSCRYSSCRFGERLLSGACRLNGRIYRLCC |
| 50 | Rat-NP-4 | Rat | ACTCRIGACVSGERLTGACGLNGRIYRLCCR |
| 51 | GPNP | Guinea pig | RRCICTTRTCRFPYRRLGTCIFQNRVYTFCC |

B. Cell Surface Receptor Binding Compounds

In some embodiments of the present invention, media for preserving organs comprise one or more cell surface receptor binding compounds. Cell surface receptor binding compounds useful in the present invention include, but are not limited to, the following broad classes of cytoactive compounds: Insulin, Insulin like Growth Factors such as IGF-I, IGF-II, and IGF-BP; Epidermal Growth Factors such as α-EGF and β-EGF; EGF-like molecules such as Keratinocyte-derived growth factor (which is identical to KAF, KDGF, and amphiregulin) and vaccinia virus growth factor (VVGF); Fibroblast Growth Factors such as FGF-1 (Basic FGF Protein), FGF-2 (Acidic FGF Protein), FGF-3 (Int-2), FGF-4 (Hst-1), FGF-5, FGF-6, and FGF-7 (identical to KGF); FGF-Related Growth Factors such as Endothelial Cell Growth Factors (e.g., ECGF-α and ECGF-β); FGF— and ECGF-Related Growth Factors such as Endothelial cell stimulating angiogenesis factor and Tumor angiogenesis factor, Retina-Derived Growth Factor (RDGF), Vascular endothelium growth factor (VEGF), Brain-Derived Growth Factor (BDGF A- and -B), Astroglial Growth Factors (AGF 1 and 2), Omentum-derived factor (ODF), Fibroblast-Stimulating factor (FSF), and Embryonal Carcinoma-Derived Growth Factor; Neurotrophic Growth Factors such as α-NGF, β-NGF, γ-NGF, Brain-Derived Neurotrophic Factor (BDNF), Neurotrophin-3, Neurotrophin-4, and Ciliary Nuerotrophic Factor (CNTF); Glial Growth Factors such as GGF-I, GGF-II, GGF-III, Glia Maturation Factor (GMF), and Glial-Derived Nuerotrophic Factor (GDNF); Organ-Specific Growth Factors such as Liver Growth Factors (e.g., Hepatopoietin A, Hepatopoietin B, and Hepatocyte Growth Factors (HCGF or HGF), Prostate Growth Factors (e.g., Prostate-Derived Growth Factors [PGF] and Bone Marrow-Derived Prostate Growth Factor), Mammary Growth Factors (e.g., Mammary-Derived Growth Factor 1 [MDGF-1] and Mammary Tumor-Derived Factor [MTGF]), and Heart Growth Factors (e.g., Nonmyocyte-Derived Growth Factor [NMDGF]); Cell-Specific Growth Factors such as Melanocyte Growth Factors (e.g., Melanocyte-Stimulating Hormone [α-, β-, and γ-MSH] and Melanoma Growth-Stimulating Activity [MGSA]), Angiogenic Factors (e.g., Angiogenin, Angiotropin, Platelet-Derived ECGF, VEGF, and Pleiotrophin), Transforming Growth Factors (e.g., TGF-α, TGF-β, and TGF-like Growth Factors such as TGF-$\beta_2$, TGF-$\beta_3$, TGF-e, GDF-1, CDGF and Tumor-Derived TGF-β-like Factors), ND-TGF, and Human epithelial transforming factor [h-TGFe]); Regulatory Peptides with Growth Factor-like Properties such as Bombesin and Bombesin-like peptides (e.g., Ranatensin, and Litorin], Angiotensin, Endothelin, Atrial Natriuretic Factor, Vasoactive Intestinal Peptide, and Bradykinin; Cytokines such as the interleukins IL-1 (e.g., Osteoclast-activating factor [OAF], Lymphocyte-activating factor [LAF], Hepatocyte-stimulating factor [HSF], Fibroblast-activating factor [FAF], B-cell-activating factor [BAF], Tumor inhibitory factor 2 [TIF-2], Keratinocyte-derived T-cell growth factor [KD-TCGF]), IL-2 (T-cell growth factor [TCGF], T-cell mitogenic factor [TCMF]), IL-3 (e.g., Hematopoietin, Multipotential colony-stimulating factor [multi-CSF], Multilineage colony-stimulating activity [multi-CSA], Mast cell growth factor [MCGF], Erythroid burst-promoting activity [BPA-E], IL-4 (e.g., B-cell growth factor I [BCGF-I], B-cell stimulatory factor 1 [BSF-1]), IL-5 (e.g., B-cell growth factor II [BCGF-II], Eosinophil colony-stimulating factor [Eo-CSF], Immunoglobulin A-enhancing factor [IgA-EF], T-cell replacing factor [TCRF]), IL-6 (B-cell stimulatory factor 2 [BSF-2], B-cell hybridoma growth factor [BCHGF], Interferon $\beta_2$ [IFN-B], T-cell activating factor [TAF], IL-7 (e.g., Lymphopoietin 1 [LP-1], Pre-B-cell growth factor [pre-BCGF]), IL-8 (Monocyte-derived neutrophil chemotactic factor [MDNCF], Granulocyte chemotatic factor [GCF], Neutrophil-activating peptide 1 [NAP-1], Leukocyte adhesion inhibitor [LAI], T-lymphocyte chemotactic factor [TLCF]), IL-9 (e.g., T-cell growth factor III [TCGF-III], Factor P40, MegaKaryoblast growth factor (MKBGF), Mast cell growth enhancing activity [MEA or MCGEA]), IL-10 (e.g., Cytokine synthesis inhibitory factor [CSIF]), IL-11 (e.g., Stromal cell-derived cytokine [SCDC]), IL-12 (e.g., Natural killer cell stimulating factor [NKCSF or NKSF], Cytotoxic lymphocyte maturation factor [CLMF]), TNF-α (Cachectin), TNF-β (Lymphotoxin), LIF (Differentiation-inducing factor [DIF], Differentiation-inducing activity [DIA], D factor, Human interleukin for DA cells [HILDA], Hepatocyte stimulating factor III [HSF-III], Cholinergic neuronal differentiation factor [CNDF], CSF-1 (Macrophage colony-stimulating factor [M-CSF]), CSF-2 (Granulocyte-macrophage colony-stimulating factor [GM-CSF]), CSF-3 (Granulocyte colony-stimulating factor [G-CSF]), and erythropoietin; Platelet-derived growth factors (e.g., PDGF-A, PDGF-B, PDGF-AB, p28-sis, and p26-cis), and Bone Morphogenetic protein (BMP), neuropeptides (e.g., Substance P, calcitonin gene-regulated peptide, and neuropeptide Y), and neurotransmitters (e.g., norepinephrine and acetylcholine).

In some preferred embodiments, EGF, IGF-1, and/or NGF are included in the media at a concentration of about 1 ng/ml to 100 ng/ml, most preferably about 10 ng/ml. In other preferred embodiments, substance P is included at a concentration of about 0.1 µg/ml to 100 µg/ml, most preferably about 2.5 µg/ml. In some embodiments, NGF is deleted as it may not be essential for suppressing delayed graft function. In some embodiments, the cell surface receptor binding compound is included in the media at a concentration sufficient to lower serum creatinine levels in kidney transplant recipients as compared to recipients of kidneys stored without cell surface receptor binding compounds. In other embodiments, the cell surface receptor binding compound(s) are included in the media at concentrations sufficient to cause a decrease in delayed graft function rates of kidneys stored in the media as compared to unsupplemented media. Preferably, the time for return to baseline serum creatinine levels is improved by at least 25%, and most preferably by at least 50%, as compared to control unsupplemented media.

Suitable cell surface receptor binding compounds may be obtained from commercial sources, purified from natural sources, or be produced by recombinant methods. Recombinant cell surface receptor binding compounds can be produced from wild-type coding sequences or from variant sequences that encode functional cell surface receptor binding compounds. Suitable cell surface receptor binding compounds also include analogs which may be smaller peptides or other molecules having similar binding and biological activity as the natural cell surface receptor binding compounds. Methods for producing cell surface receptor binding compounds are described in U.S. Pat. Nos. 5,183,805; 5,218,093; 5,130,298; 5,639,664; 5,457,034; 5,210,185; 5,470828; 5,650,496; 5,998,376; and 5,410,019; all of which are incorporated herein by reference.

C. Other Transplant Media Components

In certain embodiments, a number of other components are utilized in the media of the present invention to provide the proper balance of electrolytes, a physiological pH, proper oncotic pressure, etc. Therefore, it is contemplated that the media comprises one or more components selected from one or more of the following general groups: 1) electrolytes; 2) oncotic agents; 3) buffers; 4) energy sources; 5) impermeant anions; 6) free radical scavengers; and/or 7) ATP sources. Examples of these components are provided below along with several exemplary media formulations. Examples of media that can be supplemented with defensins include VIASPAN (U.S. Pat. Nos. 4,798,824; 4,873,230; and 5,696,152, each of which is incorporated herein by reference) and various HYPOTHERMOSOL formulations (U.S. Pat. Nos. 5,514,536 and 6,045,990, each of which is incorporated herein by reference).

1) Electrolytes

In some embodiments of the present invention, the media comprises electrolytes (e.g., sodium, potassium, calcium, magnesium, chloride, sulfate, bicarbonate, and phosphate) in concentrations approximating those found in blood plasma. For example, in some embodiments, potassium and phosphate are provided as $KH_2PO_4$ in range from about 10 to 50 mM, preferably about 25 mM; magnesium is provided as magnesium gluconate in a range of from about 1 to 10 mM, preferably about 5 mM; sodium is provided as sodium gluconate in a range of from about 50 mM to about 150 mM, preferably about 105 mM; and calcium and chloride are provided as $CaCl_2$ in a range of from about 0.1 to 5.0 mM, preferably about 0.5 mM.

In other embodiments, the concentration of individual electrolytes may be varied from physiological concentrations. For example, it is known that membrane pumps of cells are turned off during hypothermia. As a result, potassium and sodium exchange passively across the cell membrane. The media can be adjusted to compensate for the influx of sodium and efflux of potassium by providing potassium in a range of from about 35 to 45 mM and sodium in a range of from about 80 to 120 mM. In further embodiments of the present invention, divalent cations can be included in an amount sufficient to displace or block the effect of calcium ions at the cellular membrane. Accordingly, in some embodiments, $Ca^{++}$ is provided in a range of from about 0.01 mM to 0.1 mM, preferably from about 0.01 to 0.07 mM, and $Mg^{++}$ is provided in a range of from about 1 mM to 10 mM, preferably about 2.5 mM to 7.5 mM.

2) Oncotic Agents

In some embodiments of the present invention, the media comprises one or more oncotic agents. In preferred embodiments, the oncotic agent is included in an amount sufficient to maintain oncotic pressure equivalent to that of blood plasma. The present invention is not limited to any particular oncotic agent. Indeed, any oncotic agent can be used that is of a size that does not readily escape the circulation by traversing the fenestrations of the capillary bed. Examples of oncotic agents include, but are not limited to, hydroxyethyl starch, cyclodextrins, and dextran (e.g., Dextran 30, 40, or 50). In preferred embodiments, the media comprises from about 1% to 10% of the oncotic agent. In particularly preferred embodiments, the media comprises about 5% of the oncotic agent. Surprisingly, it has been found that the hydroxyethyl starch component of VIASPAN can be deleted and good results still obtained.

3) Buffers

In some embodiments of the present invention, the media comprises at least one buffer. In preferred embodiments, the concentration of buffer(s) is sufficient to maintain the pH of the media at a range of from about 7.0 to 8.0 at 10° C., preferably from about 7.4 to 7.8. The present invention is not limited to the use of any particular buffer. Indeed, the use of a variety of synthetic and other buffers is contemplated. Examples of suitable buffers include, but are not limited to, N-2-hydroxyethylpiperazine-N'-2-hydroxypropanesulfonic acid (HEPES), 3-(N-morpholino)propanesulfonic acid (MOPS), N-tris(hydroxymethyl)methyl-2-aminoethanesulfonic acid; 2-((2-hydroxy-1,1-bis(hydroxymethyl)ethyl) amino)ethanesulfonic acid (TES), 3-(N-tris(hydroxy-methyl)methylamino)-2-hydroxypropanesulfonic acid (TAPSO), 4-(2-hydroxyethyl)-1-piperazinepropanesulfonic acid (EPPS), pH range 7.3-8.7, and tris(hydroxymethyl)aminomethane (THAM), $HCO_3$, and $H_2PO_4$.

4) Energy Sources

In some embodiments of the present invention, the media further comprises one or more energy or nutrition sources. Examples of energy sources include, but are not limited to, sucrose, fructose, glucose, and dextran. Preferably, the concentration of the energy source is from about 1 mM to 20 mM, most preferably about 10 mM.

5) Impermeant Anions

In some embodiments of the present invention, the media comprises one or more impermeant anions. The impermeant anion is included to counteract swelling during cold exposure. The present invention is not limited to any particular impermeant anion. Indeed, a variety of impermeant anions are contemplated, including, but not limited to, gluconate and lactobionate. Preferably, the concentration of the impermeant anion is from about 50 to 150 mM, most preferably about 100 mM.

6) Free Radical Scavengers

In some embodiments of the present invention, the media comprises a free radical scavenger. The present invention is not limited to any particular free radical scavenger. Indeed, a variety of free radical scavengers are contemplated including, but not limited to, mannitol and glutathione. Preferably, the concentration of the free radical scavenger is from about 1 mM to 10 mM, most preferably about 3 mM.

7) ATP Substrate

In some embodiments of the present invention, the media comprises one or more ATP substrates for the regeneration of ATP during rewarming. The present invention is not limited to any particular ATP substrate. Indeed, a variety of ATP substrates are contemplated, including, but not limited to, adenosine, fructose, adenine, and ribose. Preferably, the concentration of the ATP substrate is from about 1 mM to 10 mM, most preferably about 5 mM.

8) Osmotic Agents

In some embodiments of the present invention, the media comprises one or more osmotic agents. Examples of osmotic agents include, but are not limited to, trehalose (α-α-trehalose dihydrate), raffinose, sucrose and mannitol. In preferred embodiments, the osmotic agent is provided at a concentration of about 1 mM to 100 mM, most preferably about 30 mM. In other embodiments, it is contemplated that trehalose is included in the media as protectant. Accordingly, in some embodiments, the media comprises trehalose at a concentration of about 1 mM to 30 mM, preferably about 20 mM. In other embodiments, trehalose is included in the media at a concentration sufficient to lower serum creatinine levels in kidney transplant recipients as compared to recipients of kidneys stored without antimicrobial peptides.

9) Other Components

In some embodiments of the present invention, the media may further comprise a variety of additional components. For example, in some embodiments, the media comprises an inhibitor of xanthine oxidase (e.g., allopurinol at a concentration of about 0.1 mM to 5 mM, most preferably about 1 mM). In still further embodiments, the media comprises an iron-chelating agent (e.g., deferoxamine at a concentration of from about 0.05 mM to 5 mM, most preferably about 1.0 mM). In additional embodiments, the media comprises a steroidal agent (e.g., dexamethasone at a concentration of about 1 to 30 mg/liter, most preferably about 16 mg/liter). In other embodiments, the media comprises hydrocortisone (e.g., at a concentration of from about 10 ng/ml to 100 ng/ml, preferably about 36 ng/ml). In still other embodiments, the media comprises ITS (insulin [5 μg/ml], transferrin [5 μg/ml], and selenium [5 ng/ml]). In some embodiments, the media comprises vitamin C (e.g., at about $1 \times 10^{-7}$ M). In other embodiments, the media comprises protease inhibitors (e.g., phosphoramidon [5 μM], thiorphan [1 μM], bacetracin [1 μM], and encaptopril [5 μM]).

Additionally, the media of the present invention may comprise additional cytoskeleton stabilizing agents. In particular, agents such as taxol, discodermolide, epothilone A and B, vinblastine, and vinchristine may be utilized in some embodiments of the present invention, in combination with either the antimicrobial polypeptides or cell surface receptor binding compounds or both. The use of taxol with UW solution is described in U.S. Pat. No. 5,696,152, incorporated herein by reference.

10) Exemplary Media Formulations

It is contemplated that antimicrobial peptides, other pore forming agents, and/or cell surface receptor binding compounds can be added to a variety of media formulations currently being used for organ preservation and/or other surgical procedures such as cardioplegia. Non-limiting examples of these media are provided in the Tables below. It will be recognized that the media may comprise one or more antimicrobial polypeptides (e.g., a defensin such as BNP-1). The media described below may also comprise one or more trophic factors and/or cell surface receptor binding compounds as described above. Accordingly, in some preferred embodiments, the media is supplemented with one or more of the following trophic factors: trehalose (Sigma, St. Louis Mo.; e.g., about 15 mM), substance P (Sigma; e.g., about 10 μg/ml), IGF-1 (Collaborative Biologicals; e.g., about 10 ng/ml), EGF (Sigma; e.g., about 10 ng/ml), and NGF (Sigma [murine] or Genentech [human]; e.g., about 200 ng/ml). In some preferred embodiments, the transplant media is also supplemented with dexamethasone (1-20 mg/l, preferably 8 mg/l), penicillin (20,000-500,000 units, preferably 200,000 units), and insulin (1-200 units, preferably 40 units) prior to use. In some embodiments, an antimicrobial polypeptide is not included in the medium. In some embodiments, the antimicrobial polypeptide and/or cell surface receptor binding compounds are included in the media at concentrations sufficient to lower serum creatinine levels in kidney transplant recipients as compared to recipients of kidneys stored in control unsupplemented media. In other embodiments, the antimicrobial polypeptide and/or cell surface receptor binding compounds are included in the media at concentrations sufficient to cause a decrease in delayed graft function rates of kidneys stored in the media as compared to control unsupplemented media. Preferably, the time for return to baseline serum creatinine levels is improved by at least 25%, and most preferably by at least 50%, as compared to control unsupplemented media.

It is contemplated that the media can be provided in a pre-formulated form (which can be in kit format with instructions, etc.) which comprises the antimicrobial polypeptide and/or one or more trophic factors or as a kit comprising at least one container of base medium (e.g., UW solution (VI-ASPAN), HTK Solution, EuroCollins Solution, or Collins Solution)) and a separate container or containers containing at least one of the antimicrobial polypeptides and/or one or more cell surface receptor binding compounds. Therefore, it will be recognized that the Tables below provide formulations for exemplary supplemented media (i.e., the formula of the media after addition of the antimicrobial polypeptide and at least one cell surface receptor binding compound) and that the media can be provided in either a pre-formulated form or supplemented immediately prior to use. In preferred embodiments, the antimicrobial polypeptide and/or one or more cell surface receptor binding compounds are provided in stable form that can be reconstituted. Methods for stabilization include lyophilization. In embodiments where the antimicrobial polypeptide and/or one or more cell surface receptor binding compounds are provided in lyophilized form, they can conveniently reconstituted prior to use in sterile water or in an aliquot of base medium (e.g., UW solution) prior to addition to the base medium (e.g., UW solution). In some embodiments, the kits include instructions for reconstitution of the antimicrobial polypeptide and/or one or more cell surface receptor binding compounds and/or for the use of the supplemented medium for cold storage or machine perfusion of an organ.

Alternatively, the at least one microbial polypeptide and/or one or more cell surface receptor binding compounds can be provided as a separate composition (i.e., a "bullet") that is added to a base medium. In preferred embodiments, the bullet contains a defensin and/or one or more of the cell surface receptor binding compounds described above. In some embodiments, the bullet contains a defensin and/or one or more of the cell surface receptor binding compounds above in concentrations that provide the appropriate concentration when added to one liter, two liters, or five liters of the base medium. For example, in some preferred embodiments, a bullet for addition to 1 liter of base medium comprises 1 mg of an antimicrobial polypeptide (e.g., BNP-1), 10 mg Substance P, 10 μg IGF-1, 10 μg EGF, 200 μg NGF, and an amount of trehalose sufficient to provide a concentration of 15 mM. In other preferred embodiments, a bullet for addition to 1 liter of base medium comprises 1 mg of an antimicrobial polypeptide (e.g., BNP-1), 10 mg Substance P, 10 μg IGF-1, and 10 μg EGF. In still other preferred embodiments, the antimicrobial polypeptide and/or one or more cell surface receptor binding compounds are provided in amounts such when the bullet is added to a base transplant medium and the supplemented medium is used for kidney storage prior to transplantation, subjects receiving the kidneys stored in the supplemented medium exhibit a faster return to baseline serum creatinine levels than patients receiving kidneys stored in unsupplemented medium.

TABLE 3

Supplemented UW Solution (VIASPAN)

| | |
|---|---|
| Lactobionic acid | 100 mM |
| KOH | 100 mM |
| NaOH | 20 mM |
| Adenosine | 5 mM |
| Allopurinol | 1 mM |
| Potassium Phosphate (Monobasic) | 25 mM |
| MgSO$_4$ | 5 mM |
| Raffinose | 30 mM |
| Glutathione | 3 mM |
| Hydroxyethyl starch | 50 g/L |
| Defensin | 1 mg/L |
| dexamethasone | 8 mg/l |
| penicillin | 200,000 units |
| insulin | 40 units |
| pH | 7.4 |

TABLE 4

Supplemented UW Machine Perfusion Solution

| | |
|---|---|
| Hydroxyethyl starch | 50 g/L |
| Potassium gluconate | 10 mM |
| Sodium gluconate | 90 mM |
| Potassium Phosphate (Monobasic) | 15 mM |
| Glucose | 10 mM |
| Glutathione | 3 mM |
| HEPES | 10 mM |
| Magnesium gluconate | 5 mM |
| Calcium chloride | 0.5 mM |
| Ribose | 5 mM |
| Adenosine | 5 mM |
| Adenine | 5 mM |
| Allopurinol | 1 mM |
| Mannitol | 14 mM |
| Defensin | 1 mg/L |
| pH | 7.4 |
| Osmolarity | 310 |

TABLE 5

Hypertonic Citrate Solution

| | |
|---|---|
| Na$^+$ | 80 mM |
| K$^+$ | 80 mM |
| Mg$^{++}$ | 35 mM |
| Citrate$^-$ | 55 mM |
| SO$_4^-$ | 35 mM |
| Mannitol | 136 mM |
| Defensin | 1 mg/L |
| pH | 7.1 |
| Osmolarity | 400 |

TABLE 6

HTK Solution

| | |
|---|---|
| Na$^+$ | 15 mM |
| K$^+$ | 10 mM |
| Mg$^{++}$ | 4 mM |
| Cb$^-$ | 50 mM |

TABLE 6-continued

HTK Solution

| | |
|---|---|
| Tryptophan | 2 mM |
| 2-oxoglutarate | 1 mM |
| Mannitol | 30 mM |
| Histidine | 0.18 mM |
| Histidine HCl | 18 mM |
| pH | 7.3 |
| Defensin | 1 mg/L |
| Osmolarity | 310 |

TABLE 7

HTK Solution of Bretschneider

| | |
|---|---|
| Ketoglutaric acid | 1 mM |
| Tryptophan | 2 mM |
| MgCl$_2$ | 4 mM |
| KCl | 10 mM |
| NaCl | 15 mM |
| Histidine | 200 mM |
| Defensin | 1 mg/L |
| pH | 7.3 |

TABLE 8

Phosphate Buffered Sucrose

| | |
|---|---|
| Sodium Phosphate Dibasic | 53.6 mM |
| Sodium Phosphate Monobasic | 15.5 mM |
| Sucrose | 140 mM |
| Defensin | 1 mg/L |
| pH | 7.2 |

TABLE 9

EuroCollins Solution

| | |
|---|---|
| NaHCO$_3$ | 10 mM |
| KCl | 15 mM |
| K$_2$HPO$_4$ | 42.5 mM |
| KH$_2$PO$_4$ | 15.1 mM |
| Glucose | 195 mM |
| Defensin | 1 mg/L |

TABLE 10

Collins C2 Solution

| | |
|---|---|
| K$_2$HPO$_4$ | 42.5 mM |
| KH$_2$PO$_4$ | 15.1 mM |
| KCl | 15 mM |
| NaHCO$_3$ | 10 mM |
| Glucose | 140 mM |
| MgSO$_4$ | 30 mM |
| Defensin | 1 mg/L |

TABLE 11

Supplemented UW Solution (VIASPAN)

| | |
|---|---|
| Lactobionic acid (potassium lactobionate) | 100 mM |
| KOH | 100 mM |
| NaOH | 20 mM |

TABLE 11-continued

| Supplemented UW Solution (VIASPAN) | |
|---|---|
| Adenosine | 5 mM |
| Allopurinol | 1 mM |
| Potassium Phosphate (Monobasic) | 25 mM |
| MgSO$_4$ | 5 mM |
| Raffinose | 30 mM |
| Glutathione | 3 mM |
| Hydroxyethyl starch | 50 g/L |
| BNP-1 | 1 mg/L |
| Trehalose | 15 mM |
| Substance P | 10 µg/ml |
| IGF-1 | 10 ng/ml |
| EGF | 10 ng/ml |
| NGF | 200 ng/ml |
| dexamethasone | 8 mg/l |
| penicillin | 200,000 units |
| insulin | 40 units |
| pH | 7.4 |

TABLE 12

| Supplemented UW Solution (VIASPAN) | |
|---|---|
| Lactobionic acid (potassium lactobionate) | 100 mM |
| KOH | 100 mM |
| NaOH | 20 mM |
| Adenosine | 5 mM |
| Allopurinol | 1 mM |
| Potassium Phosphate (Monobasic) | 25 mM |
| MgSO$_4$ | 5 mM |
| Raffinose | 30 mM |
| Glutathione | 3 mM |
| Hydroxyethyl starch | 50 g/L |
| BNP-1 | 1 mg/L |
| Substance P | 10 µg/ml |
| IGF-1 | 10 ng/ml |
| EGF | 10 ng/ml |
| dexamethasone | 8 mg/l |
| penicillin | 200,000 units |
| insulin | 40 units |
| pH | 7.4 |

TABLE 13

| EuroCollins Solution | |
|---|---|
| NaHCO$_3$ | 10 mM |
| KCl | 15 mM |
| K$_2$HPO$_4$ | 42.5 mM |
| KH$_2$PO$_4$ | 15.1 mM |
| Glucose | 195 mM |
| Trehalose | 15 mM |
| Substance P | 10 µg/ml |
| IGF-1 | 10 ng/ml |
| EGF | 10 ng/ml |
| NGF | 200 ng/ml |
| BNP-1 | 1 mg/L |
| EuroCollins Solution | |
| NaHCO$_3$ | 10 mM |
| KCl | 15 mM |
| K$_2$HPO$_4$ | 42.5 mM |
| KH$_2$PO$_4$ | 15.1 mM |
| Glucose | 195 mM |
| Substance P | 10 µg/ml |
| IGF-1 | 10 ng/ml |
| EGF | 10 ng/ml |
| BNP-1 | 1 mg/L |

TABLE 14

| Supplemented UW Solution (VIASPAN) | |
|---|---|
| Lactobionic acid (potassium lactobionate) | 100 mM |
| KOH | 100 mM |
| NaOH | 20 mM |
| Adenosine | 5 mM |
| Allopurinol | 1 mM |
| Potassium Phosphate (Monobasic) | 25 mM |
| MgSO$_4$ | 5 mM |
| Raffinose | 30 mM |
| Glutathione | 3 mM |
| Hydroxyethyl starch | 50 g/L |
| Trehalose | 15 mM |
| Substance P | 10 µg/ml |
| IGF-1 | 10 ng/ml |
| EGF | 10 ng/ml |
| NGF | 200 ng/ml |
| dexamethasone | 8 mg/l |
| penicillin | 200,000 units |
| insulin | 40 units |
| pH | 7.4 |

TABLE 15

| Supplemented UW Solution (VIASPAN) | |
|---|---|
| Lactobionic acid (potassium lactobionate) | 100 mM |
| KOH | 100 mM |
| NaOH | 20 mM |
| Adenosine | 5 mM |
| Allopurinol | 1 mM |
| Potassium Phosphate (Monobasic) | 25 mM |
| MgSO$_4$ | 5 mM |
| Raffinose | 30 mM |
| Glutathione | 3 mM |
| Hydroxyethyl starch | 50 g/L |
| Substance P | 10 µg/ml |
| IGF-1 | 10 ng/ml |
| EGF | 10 ng/ml |
| dexamethasone | 8 mg/l |
| penicillin | 200,000 units |
| insulin | 40 units |
| pH | 7.4 |

TABLE 16

| EuroCollins Solution | |
|---|---|
| NaHCO$_3$ | 10 mM |
| KCl | 15 mM |
| K$_2$HPO$_4$ | 42.5 mM |
| KH$_2$PO$_4$ | 15.1 mM |
| Glucose | 195 mM |
| Trehalose | 15 mM |
| Substance P | 10 µg/ml |
| IGF-1 | 10 ng/ml |
| EGF | 10 ng/ml |
| NGF | 200 ng/ml |

TABLE 17

| EuroCollins Solution | |
|---|---|
| NaHCO$_3$ | 10 mM |
| KCl | 15 mM |
| K$_2$HPO$_4$ | 42.5 mM |
| KH$_2$PO$_4$ | 15.1 mM |
| Glucose | 195 mM |
| Substance P | 10 µg/ml |
| IGF-1 | 10 ng/ml |
| EGF | 10 ng/ml |

II. Uses of Media

It is contemplated that the media described above may be utilized in a variety of transplant and other medical procedures. It is contemplated that the media can be used for the preservation of any tissue, organ, cell(s), or organisms, including, but not limited to, organs, genetically engineered tissues, biomedically engineered tissues, sperm, eggs, and embryos. In particular, the media finds use for the preservation of both internal and external organs prior to transplant. In some embodiments, the media is utilized for hypothermic storage of the organ. In hypothermic storage, the organ is flushed with the media, cooled, suspended in the media, and stored. In other embodiments, the media is utilized for pulsatile hypothermic perfusion of the organ. In still further embodiments, the present invention provides a composition comprising an internal organ suspended in or perfused with a media comprising one or more antimicrobial polypeptides (e.g., defensins) and/or at least one cell surface receptor binding protein. In particularly preferred embodiments, the media of the present invention are useful for decreasing the incidence and/or severity of delayed graft function in patients receiving transplanted kidneys stored and/or treated with the media of the present invention.

In other embodiments, the present invention provides a composition comprising skin or another external organ suspended in or perfused with a media comprising an antimicrobial peptide or other pore forming agents and/or at least one growth factor. In other embodiments, the media may be used in procedures such as cardioplegia (See, e.g., U.S. Pat. No. 5,514,536, incorporated herein by reference).

EXPERIMENTAL

The following examples serve to illustrate certain preferred embodiments and aspects of the present invention and are not to be construed as limiting the scope thereof.

Example 1

This Example describes the use of media comprising defensins for the storage of organs prior to transplant. The study was performed on adult beagle dogs of both sexes weighing approximately 8 kg. The study employed a kidney autotransplantation with immediate contralateral nephrectomy model. This involved harvesting of either the left or right kidney and flushing it out through the renal artery with the University of Wisconsin solution (See Table 3) either with or without added defensins (1 mg/liter), storage of the kidney under sterile conditions on ice for 3 days, reimplantation of the previously harvested kidney into the abdominal cavity of the same dog and then immediately removing the other kidney.

For harvest of the kidney, a midline abdominal incision was made and the left kidney isolated by dissecting free of any attachments to its artery, vein and ureter. The ureter was ligated with a single 4-0 silk ligature near the bladder and divided proximal to the ligature. The gonadal vein was ligated with 2 4-0 silk ligatures and divided. The renal artery and vein were then clamped and cut and the kidney removed for vascular flushing with preservation solution and experimental storage. The kidney was then suspended in preservation solution in sterile plastic bags and placed on ice in a cooler for storage. The stumps of the renal artery and vein were ligated separately with doubled 3-0 silk ligatures. The excision site was inspected for hemorrhage and any small bleeders were cauterized or ligated. The body wall was closed with O-Maxon in a simple continuous pattern. The skin was then closed with 3-0 Vicryl in a simple continuous subcuticular pattern after which the dog was recovered from anesthesia.

Three days after harvest of the kidney the dog was anesthetized for reimplantation of the stored kidney. Intravenous morphine (0.5 mg/kg) was administered as prophylaxis against intussusception. The abdomen was entered through a midline abdominal incision made by opening the previous incision and extending the incision to the pubis. The external iliac artery and common iliac vein were isolated by blunt and sharp dissection. The external iliac artery was ligated distally, clamped proximally with an atraumatic vascular clamp and divided just proximal to the ligature. The free arterial end was flushed with heparinized saline and its end cleared of loose adventitia. The common iliac vein surface was cleared of loose adventitia by sharp dissection. An atraumatic vascular clamp was placed on the vein both proximally and distally and the vein wall fenestrated using a Metzenbaum scissors. The vein segment was flushed free of blood with heparinized saline. Four 7-0 polyester sutures were placed in the wall of the vein exiting the fenestration and attached to the renal vein. The renal vein was apposed to the side of the iliac vein and the anastomosis performed using two lines (front and back vessel walls) of simple continuous suture. The renal artery was apposed to the end of the external iliac artery using two 7-0 polypropylene sutures and the anastomosis completed with two lines of simple continuous suture. The proximal venous clamp was removed followed by the arterial vascular clamp. Mannitol (1 gm/kg IV) was administered during anastomosis, which required less than 30 minutes to complete. The bladder was entered through a ventral incision and fenestrated on its dorsal side with a hemostat. The ureter was incised longitudinally for 1 cm and then pulled through the bladder fenestration. The ureteral mucosa and bladder mucosa was apposed using 6-0 Vicryl suture in a continuous pattern. The bladder was closed with 3-0 Vicryl in a Cushing pattern. The contralateral kidney was excised and the ureter, renal artery, and renal vein ligated with 3-0 silk. The abdominal wall was closed with O-Maxon and the skin with 3-0 Vicryl using continuous suture patterns in the linea alba and subcuticular layers, respectively. The dog was then given 500 ml lactated Ringer's solution subcutaneously and recovered from anesthesia.

The results are presented in FIG. 1. As can be seen, dogs receiving kidneys stored for three days in UW solution supplemented with BNP-1 exhibited serum creatinine of about half that seen in dogs receiving kidneys stored in UW solution alone. This is indicative of markedly improved renal function in kidneys preserved in media containing BNP-1.

Example 2

Figure 2:
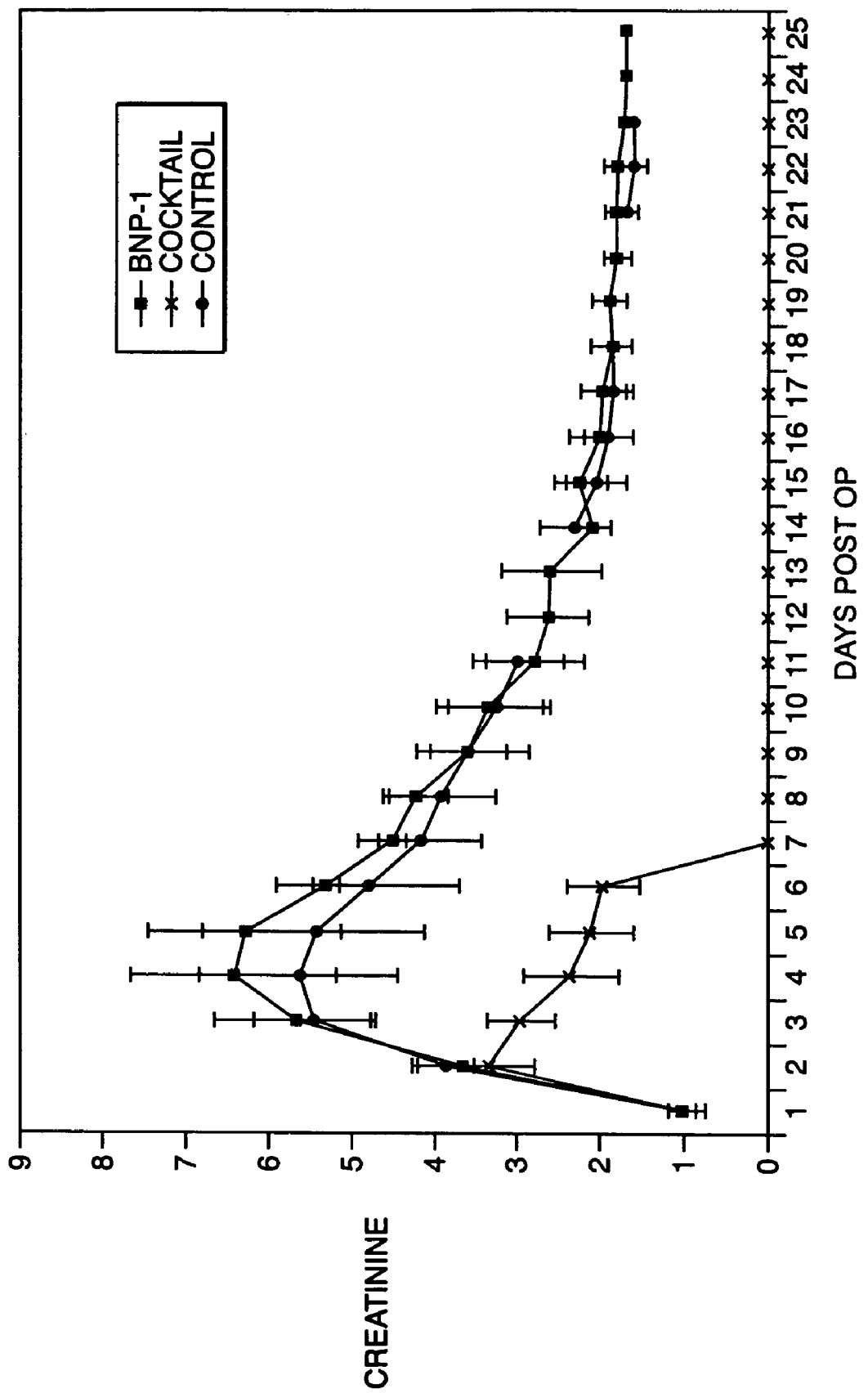
FIG. 2 is a graph showing serum creatinine levels (Y-axis) over time (X-axis) in dogs receiving kidneys stored for four days in UW solution alone (solid circles), in UW solution supplemented with BNP-1 (solid squares), or in UW solution supplemented with BNP-1 and growth factors (x's).

This Example describes the use of media comprising defensins and/or cell surface receptor binding compounds for the storage of organs prior to transplant. The study was performed as described in Example 1, except that the organs were stored for four days prior to transplant. The three test groups were UW solution alone, UW solution supplemented with 1 mg/L BNP-1 (synthesized by Multiple Peptide Systems, San Diego Calif.), and UW solution supplemented with 1 mg/L BNP-1, and the following trophic factors: 20 mM trehalose (Sigma, St. Louis Mo.), 2.5 mg/L substance P (Sigma), 10 µg/L IGF-1 (Collaborative Biologicals), 10 µg/L EGF (Sigma), and 200 ng/ml NGF (Sigma [murine] or Genentech [human])). The results are presented in FIG. 2. As can be seen, dogs receiving kidneys stored in UW solution supplemented with BNP-1 and cell surface receptor binding compounds exhibited serum creatinine of about half that seen in dogs receiving kidneys stored in UW solution supplemented with BNP-1 or UW solution alone. Surprisingly, the serum creatinine levels in the dogs receiving kidneys stored in UW solution supplemented with both BNP-1 and cell surface receptor binding compounds remarkably improved the quality of preservation to the point that they equal 3 day BNP-1 preserved kidneys and 2 day or less storage with UW solution alone.

Example 3

Figure 3:
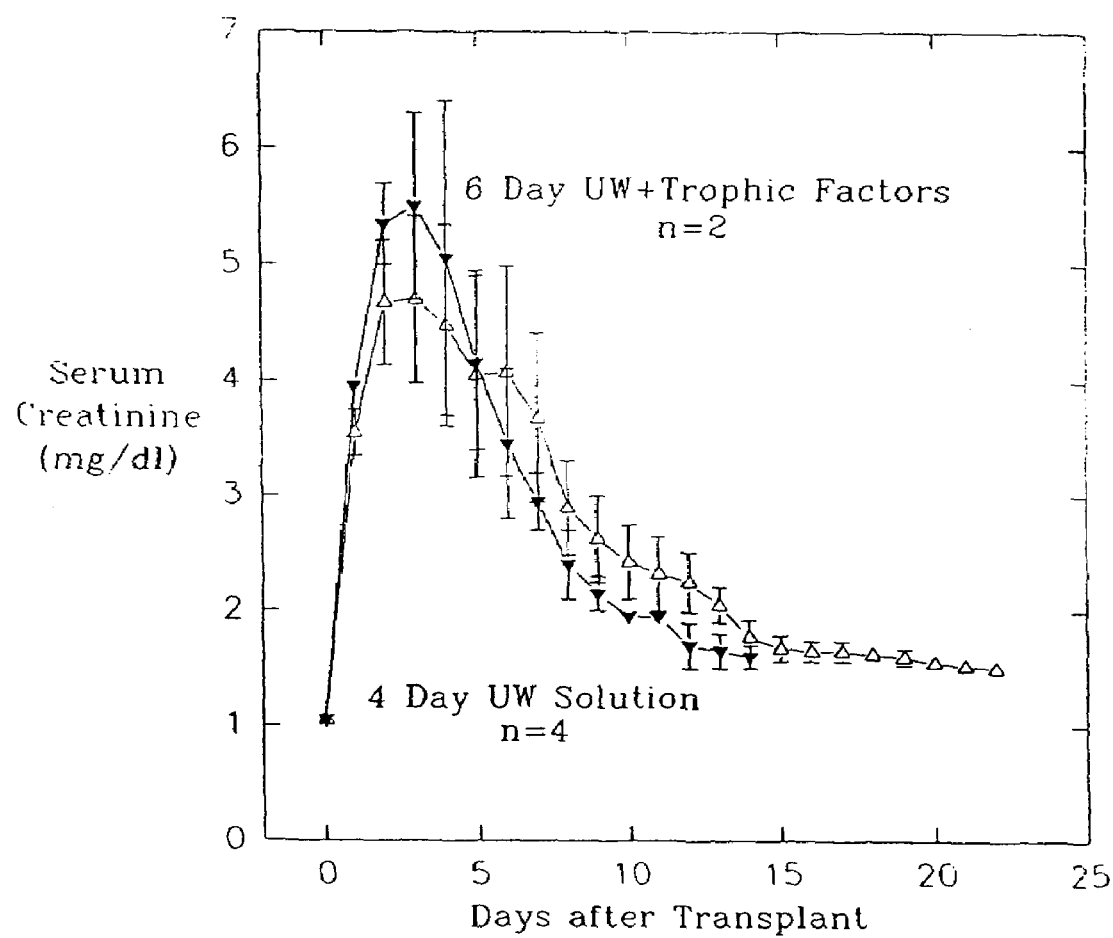
FIG. 3 is a graph showing serum creatinine levels (Y-axis) over time (X-axis) in dogs receiving kidneys stored for four days in UW solution alone (solid triangles) or six days in UW solution supplemented with trophic factors (unfilled triangles).

This Example describes results from the transplant of kidneys after six days of storage. This study was performed as described in Example 1, except that the kidneys were stored for four days in UW solution prior to transplant or six days in UW solution supplemented with a defensin and trophic factors (See Example 2) prior to transplant. The results are presented in FIG. 3. As can be seen, the serum creatinine levels following transplant were similar in the two groups. These data demonstrate that UW solution supplemented with trophic factors can be used increase the duration of storage.

Example 4

Figure 4:
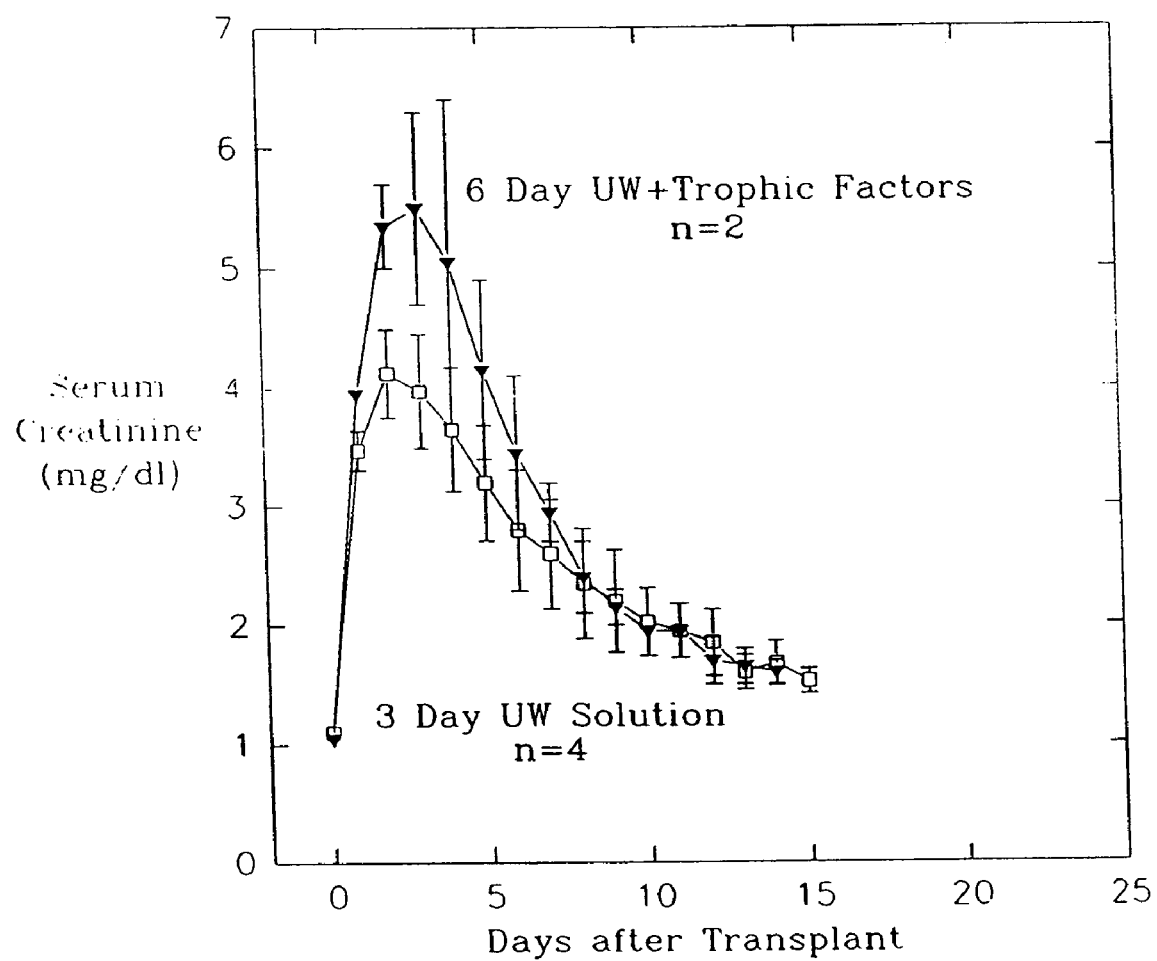
FIG. 4 is a graph showing serum creatinine levels (Y-axis) over time (X-axis) in dogs receiving kidneys stored for three days in UW solution alone (solid tangles) or six days in UW solution supplemented with trophic factors (squares).

This Example describes results from the transplant of kidneys after six days of storage. This study was performed as described in Example 3, except that the kidneys were stored for three days in UW solution prior to transplant or six days in UW solution supplemented with a defensin and trophic factors (See Example 2) prior to transplant. The results are presented in FIG. 4. As can be seen, the serum creatinine levels following transplant were higher in the dogs receiving kidneys stored for six days as opposed dogs receiving kidneys stored for three days. These data demonstrate that UW solution supplemented with trophic factors can be used increase the duration of storage.

Example 5

Figure 5:
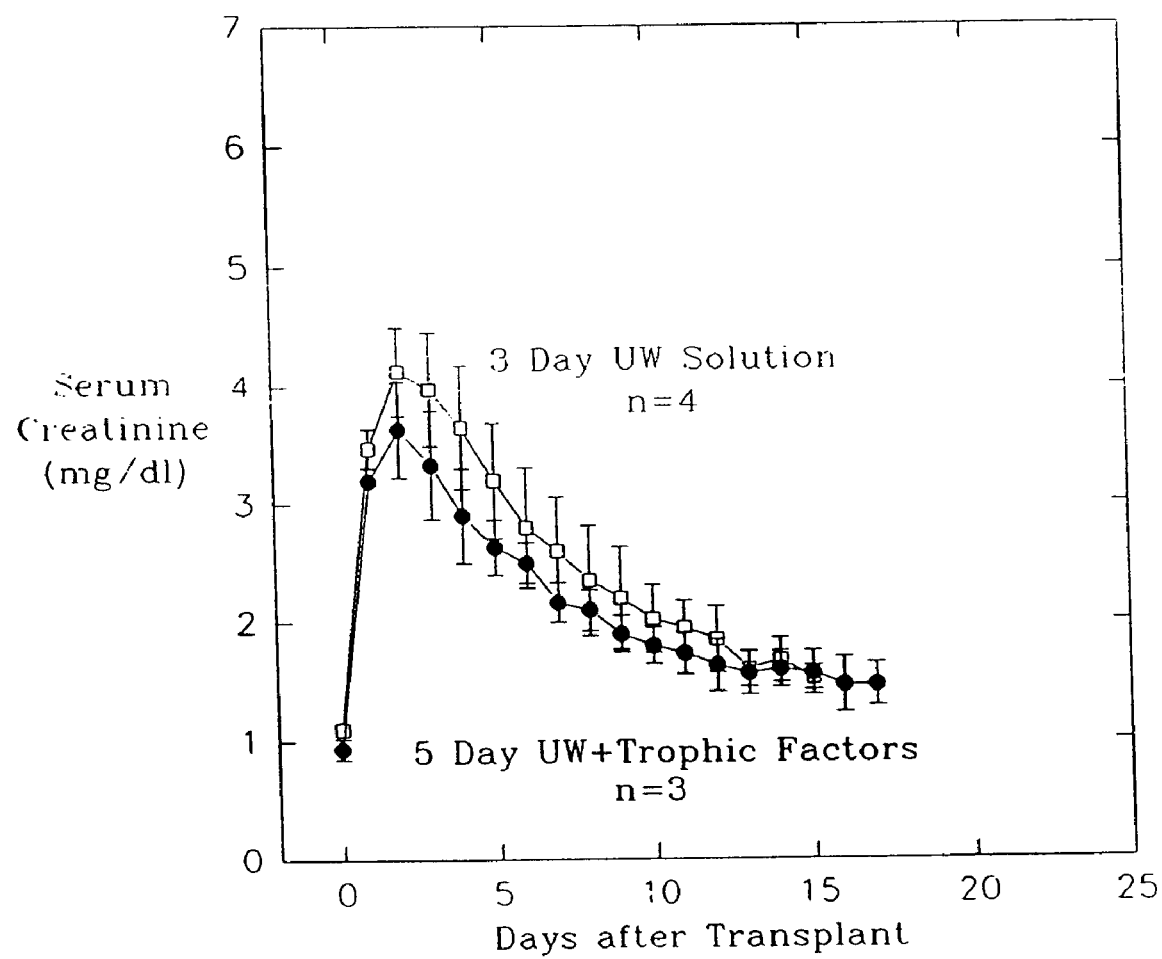
FIG. 5 is a graph showing serum creatinine levels (Y-axis) over time (X-axis) in dogs receiving kidneys stored for three days in UW solution alone (squares) or five days in UW solution supplemented with trophic factors (circles).

This Example describes the results from the transplant of kidneys after five days of storage. This study was performed as described in Example 3, except that the kidneys were stored for three days in UW solution prior to transplant or five days in UW solution supplemented with a defensin and trophic factors (See Example 2) prior to transplant. The results are presented in FIG. 5. As can be seen, the serum creatinine levels following transplant were higher in the dogs receiving kidneys stored for three days in UW solution as opposed dogs receiving kidneys stored for five days in UW solution plus trophic factors. These data demonstrate that UW solution supplemented with trophic factors can be used increase the duration of storage.

Example 6

Figure 6:
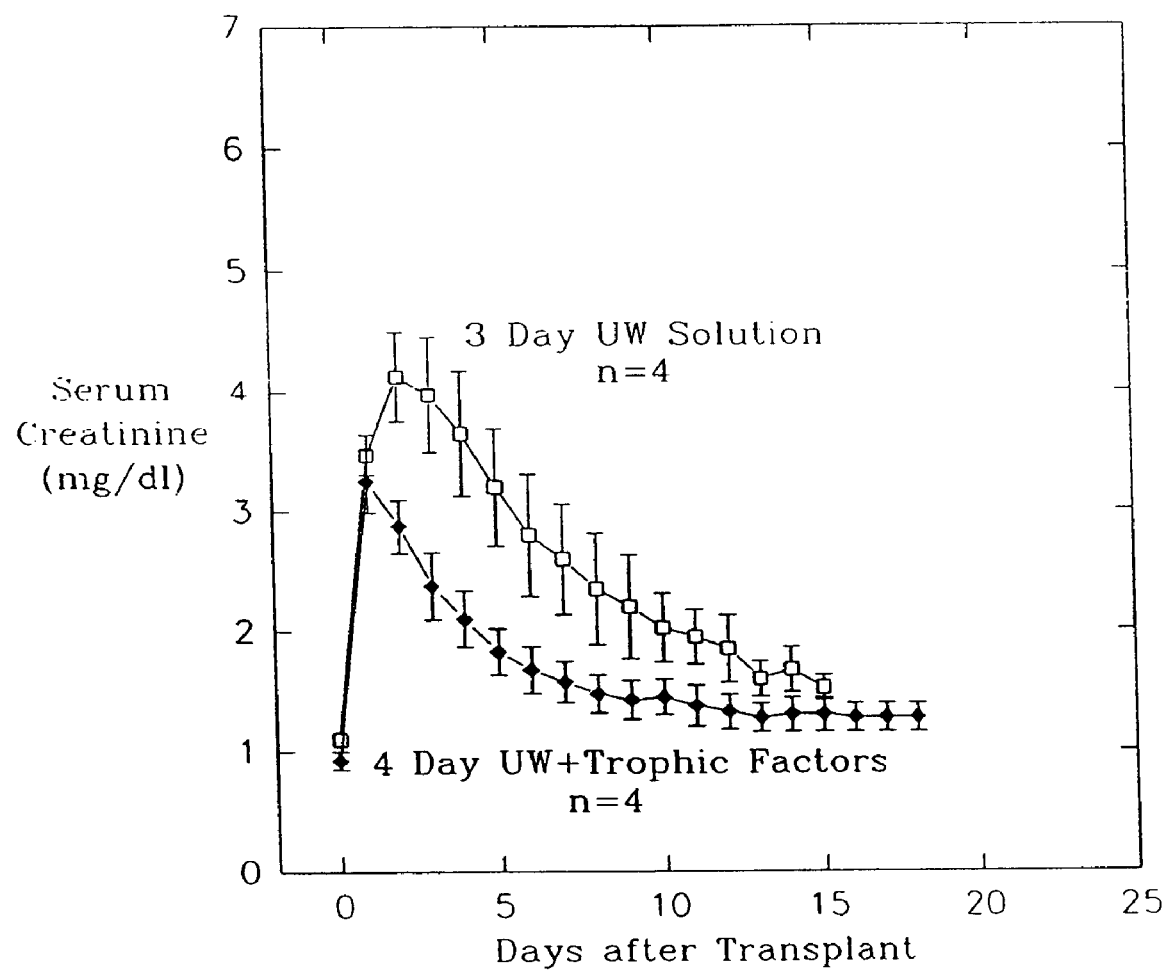
FIG. 6 is a graph showing serum creatinine levels (Y-axis) over time (X-axis) in dogs receiving kidneys stored for three days in UW solution alone (squares) or four days in UW solution supplemented with trophic factors (diamonds).

This Example describes the results from the transplant of kidneys after four days of storage. This study was performed as described in Example 3, except that the kidneys were stored for three days in UW solution prior to transplant or four days in UW solution supplemented with a defensin and trophic factors (See Example 2) prior to transplant. The results are presented in FIG. 6. As can be seen, the serum creatinine levels following transplant were significantly higher in the dogs receiving kidneys stored for three days in UW solution as opposed dogs receiving kidneys stored for four days in UW solution plus trophic factors. These data demonstrate that UW solution supplemented with trophic factors can be used increase the duration of storage are indicative of markedly improved renal function in kidneys preserved in media containing trophic factors.

Example 7

Figure 7:
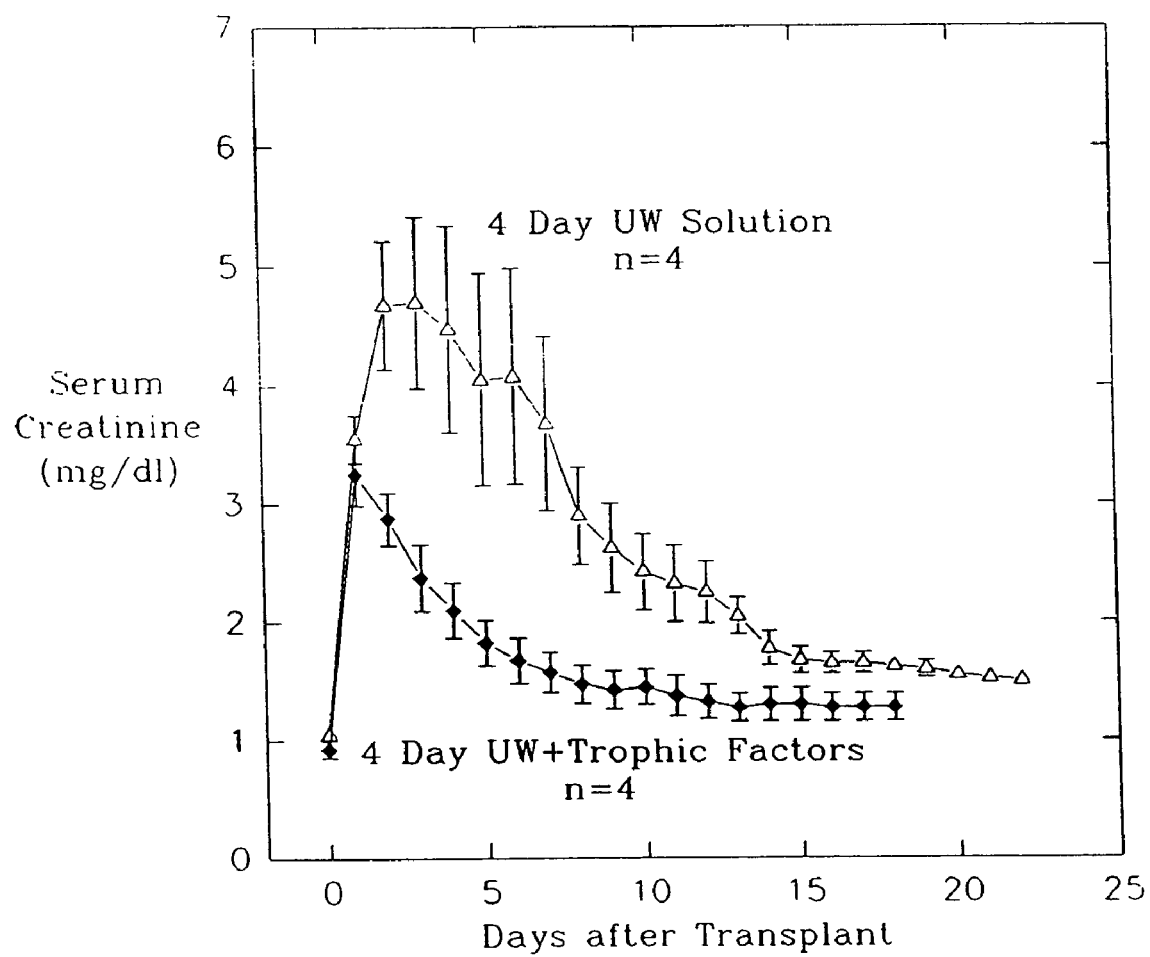
FIG. 7 is a graph showing serum creatinine levels (Y-axis) over time (X-axis) in dogs receiving kidneys stored for four days in UW solution alone (solid triangles) or four days in UW solution supplemented with trophic factors (diamonds).

This Example describes the results from the transplant of kidneys after four days of storage. This study was performed as described in Example 3, except that the kidneys were stored for four days in UW solution prior to transplant or four days in UW solution supplemented with a defensin and trophic factors (See Example 2) prior to transplant. The results are presented in FIG. 7. As can be seen, the serum creatinine levels following transplant were significantly higher in the dogs receiving kidneys stored for four days in UW solution as opposed dogs receiving kidneys stored for four days in UW solution plus trophic factors. These data are indicative of markedly improved renal function in kidneys preserved in media containing trophic factors.

Example 8

Figure 8:
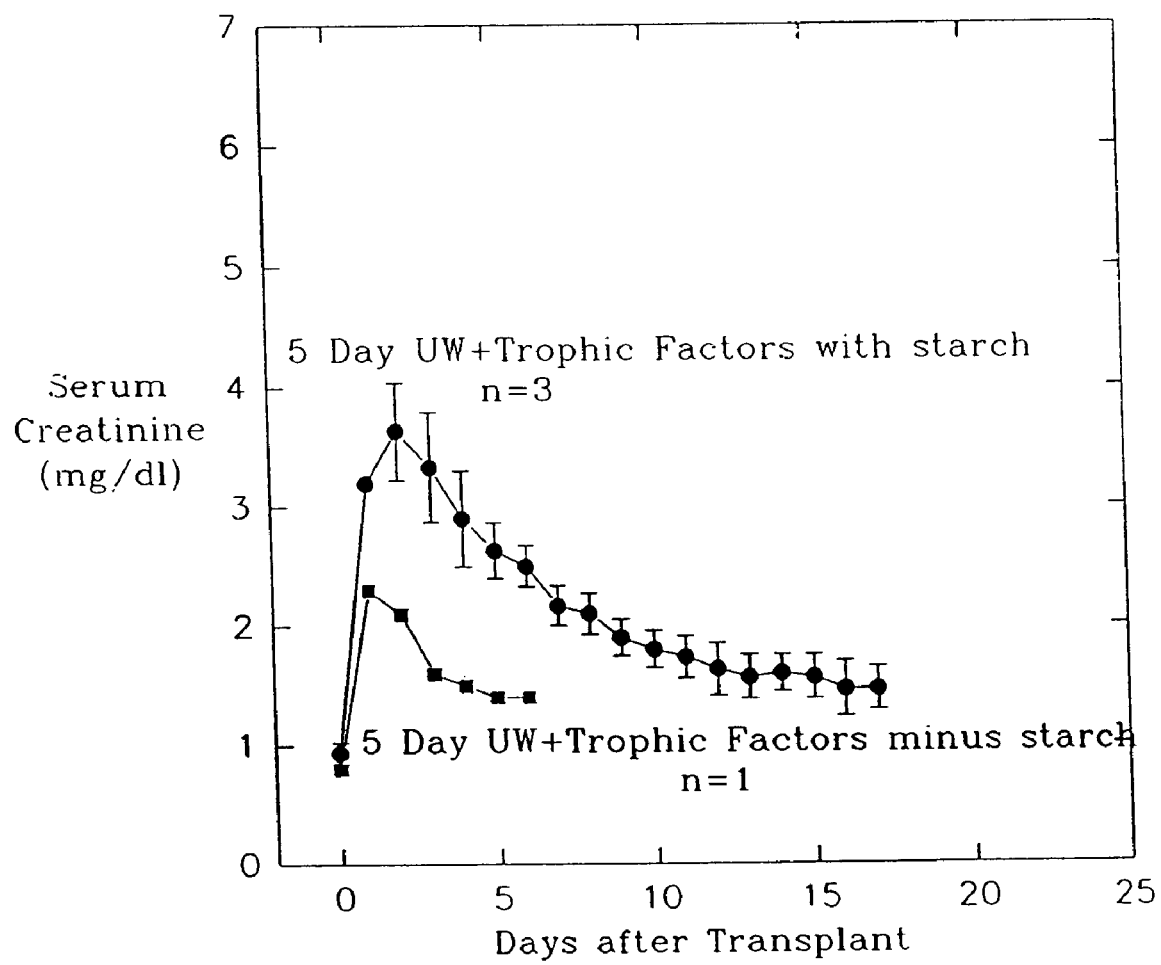
FIG. 8 is a graph showing serum creatinine levels (Y-axis) over time (X-axis) in dogs receiving kidneys stored for five days in UW solution with trophic factors and with starch (circles) or five days in UW solution supplemented with trophic factors and without starch (squares).

This Example demonstrates that hydroxyethyl starch can be deleted from UW solution without adversely affecting organ quality. This study was performed as described in Example 3, except that the kidneys were stored for five days prior to transplant in UW solution containing hydroxyethyl starch and supplemented with trophic factors or five days prior to transplant in UW solution supplemented with trophic factors (See Example 2), and in which the hydroxyethyl starch was omitted. The results are presented in FIG. 8. Surprisingly, the serum creatinine levels following transplant were significantly higher in the dogs receiving kidneys stored in UW solution containing hydroxyethyl starch as opposed dogs receiving kidneys stored in UW solution without hydroxyethyl starch.

Example 9

Figure 9:
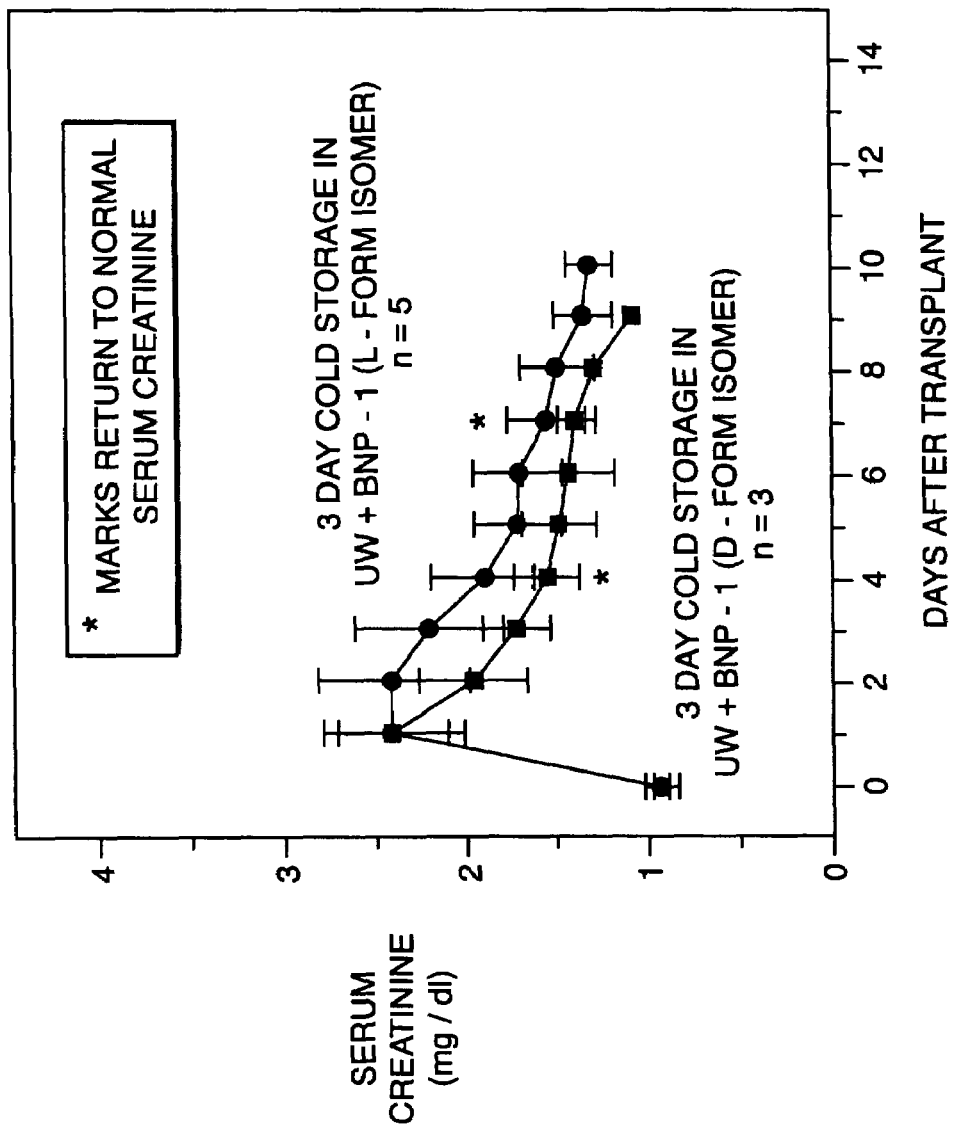
FIG. 9 is a graph showing serum creatinine levels (Y-axis) over time (X-axis) in dogs receiving kidneys stored for three days in UW solution supplemented with BNP-1 (L-form isomer)(circles) or three days in UW solution supplemented with BNP-1 (D-form isomer) (squares).

This Example demonstrates experiments where use of the D-form isomer of BNP-1 was compared with L-form isomer. The D-form isomers was synthesized with D-amino acids. This study was performed as described in Example 1, except that the kidneys were stored for three days prior to transplant in UW solution containing the L-form isomer of BNP-1 or three days prior to transplant in UW solution containing the D-form isomer of BNP-1. The results are presented in FIG. 9. As can be seen, dogs receiving kidneys stored in media supplemented with the D-form isomer returned to normal serum creatinine levels faster than dogs receiving kidneys stored in the media supplemented with the L-form isomer.

Example 10

This Example describes the effect UW solution supplemented with BNP-1 on cytoskeletal structure of kidney cells. Briefly, either MDCK cells or primary kidney cell cultures were stored for three days at cold temperatures in either UW solution, UW solution supplemented with BNP-1, or DMEM. The cells were then labeled with actin and tubulin antibodies and analyzed by confocal fluorescence microscopy. Control untreated cells displayed a homogeneous fine fibrillar pattern of actin and tubulin that extended throughout the cell. Cells stored in DMEM culture media at cold temperatures displayed nearly complete dissolution of both actin and tubulin with very little staining present. Cells stored in UW solution had nearly complete disruption of the tubulin elements and significant dissolution of the actin microfilaments. In primary cultures in UW solution, the residual actin is condensed along the plasma membrane. Treatment with BNP-1 during storage resulted in better maintenance of actin and tubulin in MDCK cells. In primary cultures with BNP-1, the tubulin and actin were better stained and more persistent with some condensation along stellate rays which extended from the nucleus out to the plasma membrane of the cells In a separate experiment, the effect of BNP-1 on the cytoskeleton after three days cold storage in UW solution followed by 3 hours warm reperfusion in DMEM culture media with 10% serum was determined. MDCK cells stored in DMEM culture media at 4° C. failed to reassemble the cytoskeleton by 3 hours of reperfusion. MDCK cells stored in UW solution and then reperfused were able to reassemble the cytoskeleton, but in primary kidney cell cultures the cytoskeleton remained abnormal at 3 hours of reperfusion. In these primary cells, the actin and tubulin filaments maintained a coarse clumpy pattern with considerable cortical condensation near the plasma membrane and only a limited amount of fine fibrillar structure that would be considered more normal. Cells stored in BNP-1 supplemented UW solution and reperfused had superior maintenance and reassembly of the cytoskeleton in both MDCK and primary renal cultures with homogeneously distributed fine fibrillar cytoskeletal elements predominating in these cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organ storgae and transplant, cryobiology, biochemistry, or related fields are intended to be within the scope of the following claims.

What is claimed is:

1. An in vitro composition comprising an internal organ at a temperature of 0-4° C., lactobionate, Substance P, nerve growth factor, and recombinant insulin-like growth factor 1, said recombinant Insulin-like Growth Factor 1 provided at a concentration of from about 1 ng/ml to 100 ng/ml.

2. The composition of claim 1, further comprising hydroxyethyl starch.

3. The composition of claim 2, wherein said hydroxyethyl starch is present in a concentration of about 1 g/l to 200 g/l.

4. The composition of claim 1, further comprising an antimicrobial polypeptide.

5. The composition of claim 4, wherein said antimicrobial polypeptide is a defensin.

6. The composition of claim 5, wherein the amino acid sequence for said defensin is SEQ ID NO: 37.

7. The composition of claim 4, wherein said antimicrobial polypeptide is present in a concentration of about 0.01 mg/l to 1000 mg/l.

8. The composition of claim 1, wherein said lactobionate is present in a concentration of about 1 mM to 500 mM.

9. The composition of claim 1, wherein said Substance P is provided at a concentration of from about 0.1 µg/ml to 100 µg/ml.

10. The composition of claim 1, wherein said Nerve Growth Factor is provided at a concentration of from about 1 ng/ml to 100 ng/ml.

11. An in vitro composition comprising an internal organ at a temperature of 0-4° C., lactobionate at a concentration of about 1 mM to 500 mM, Substance P. nerve growth factor, and recombinant insulin-like growth factor 1 at a concentration of from about 1 ng/ml to 100 ng/ml.

12. An in vitro composition comprising an internal organ, lactobionate at a concentration of about 1 mM to 500 mM, recombinant insulin-like growth factor 1 at a concentration of from about 1 ng/ml to 100 ng/ml, hydroxyethyl starch at a concentration of about 1 g/l to 200 g/l, Nerve Growth Factor at a concentration of from about 1 ng/ml to 100 ng/ml, and Substance P at a concentration of from about 0.1 µg/ml to 100 µg/ml.

\* \* \* \* \*

UNITED STATES PATENT AND TRADEMARK OFFICE
CERTIFICATE OF CORRECTION

PATENT NO. : 7,592,023 B2  Page 1 of 1
APPLICATION NO. : 10/657851
DATED : September 22, 2009
INVENTOR(S) : Murphy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 934 days.

Signed and Sealed this

Twenty-first Day of September, 2010

David J. Kappos
*Director of the United States Patent and Trademark Office*